(12) United States Patent
Knox

(10) Patent No.: US 7,947,633 B2
(45) Date of Patent: May 24, 2011

(54) POLYCATIONIC VISCOELASTIC COMPOSITIONS

(75) Inventor: Paul Knox, Kenosha, WI (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 12/846,464

(22) Filed: Jul. 29, 2010

(65) Prior Publication Data

US 2010/0311622 A1 Dec. 9, 2010

Related U.S. Application Data

(60) Division of application No. 12/098,881, filed on Apr. 7, 2008, now Pat. No. 7,772,165, which is a continuation of application No. PCT/US2006/043191, filed on Nov. 7, 2006.

(60) Provisional application No. 60/734,465, filed on Nov. 7, 2005.

(51) Int. Cl.
| | |
|---|---|
| C09K 8/04 | (2006.01) |
| C09K 8/86 | (2006.01) |
| E21B 43/267 | (2006.01) |
| C11D 3/30 | (2006.01) |
| C11D 3/48 | (2006.01) |
| C23F 11/14 | (2006.01) |

(52) U.S. Cl. ........ 507/240; 507/269; 507/272; 507/276; 507/277; 507/925; 507/927; 507/935; 166/280.2; 166/294; 510/259; 510/330; 510/384; 510/391; 252/390; 252/401; 252/175

(58) Field of Classification Search ................... 507/240
See application file for complete search history.

(56) References Cited

U.S. PATENT DOCUMENTS

| | | | |
|---|---|---|---|
| 2,792,400 A | 5/1957 | Keiser et al. | |
| 2,807,910 A | 10/1957 | Erickson | |
| 2,933,529 A | 4/1960 | Hwa | |
| 3,079,436 A | 2/1963 | Hwa | |
| 3,235,457 A * | 2/1966 | Laden | ............................ 424/65 |
| 3,661,966 A | 5/1972 | Bartmann et al. | |

(Continued)

FOREIGN PATENT DOCUMENTS

EP 0835983 12/2003

(Continued)

OTHER PUBLICATIONS

International Search Report from parent PCT application No. PCT/US06/43191; 2 pages.

(Continued)

*Primary Examiner* — Joseph D Anthony
(74) *Attorney, Agent, or Firm* — McAndrews, Held & Malloy, Ltd.

(57) ABSTRACT

Viscoelastic compositions are disclosed herein containing an effective amount of one or more random or structurally defined polycationic quaternary ammonium compounds for controlling the viscoelasticity of the composition. In at least one aspect, the present technology provides polycationic quaternary ammonium compounds comprising dissymmetric bis-quaternary compounds. In another aspect, the present technology provides viscoelastic compositions comprising polycationic quaternary ammonium compounds that comprise dissymmetric bis-quaternary compounds. In yet another aspect, the present technology provides polycationic quaternary ammonium compounds comprising a carboxylate functional polycationic quaternary ammonium compound. Preferred viscoelastic compositions of the present technology maintain viscoelasticity at a temperature greater than about 80° C., preferably greater than about 100° C. or about 110° C. when the amount of the one or polycationic quaternary compounds is less than about 10% by weight based on the total weight of the composition.

21 Claims, 15 Drawing Sheets

U.S. PATENT DOCUMENTS

| | | | |
|---|---|---|---|
| 3,932,622 A * | 1/1976 | Friedman et al. | 514/558 |
| 4,073,927 A | 2/1978 | Freilich | |
| 4,110,910 A | 9/1978 | Dombrowski | |
| 4,151,304 A * | 4/1979 | Evans | 514/777 |
| 4,534,877 A | 8/1985 | Russell et al. | |
| 4,612,188 A | 9/1986 | Zorayan et al. | |
| 4,734,277 A | 3/1988 | Login | |
| 4,812,263 A | 3/1989 | Login | |
| 4,828,819 A | 5/1989 | Lan et al. | |
| 5,196,135 A | 3/1993 | Merianos | |
| 5,258,137 A | 11/1993 | Bonekamp et al. | |
| 5,384,334 A | 1/1995 | Polovsky et al. | |
| 5,551,516 A | 9/1996 | Normal et al. | |
| 5,618,798 A * | 4/1997 | Bar-Shalom et al. | 514/53 |
| 5,643,498 A | 7/1997 | Li et al. | |
| 5,964,295 A | 10/1999 | Brown et al. | |
| 5,979,557 A | 11/1999 | Card et al. | |
| 6,436,890 B1 | 8/2002 | Kourai et al. | |
| 6,730,665 B1 | 5/2004 | Maran et al. | |
| 7,772,165 B2 * | 8/2010 | Knox | 507/240 |
| 2004/0067855 A1 | 4/2004 | Hughes et al. | |
| 2004/0102330 A1 | 5/2004 | Zhou et al. | |
| 2007/0111896 A1 | 5/2007 | Knox et al. | |

FOREIGN PATENT DOCUMENTS

| | | |
|---|---|---|
| GB | 2332224 A | 6/2003 |

OTHER PUBLICATIONS

Chang et al., Case study of a novel acid diversion technique in carbonate reservoirs, Society of Petroleum Engineers, 56529, 1999; 9 pages.

Supplemental European Search Report corresponding to European patent application Serial No. 06844281.3-2111, dated Nov. 3, 2008; 5 pages.

* cited by examiner

STEP 1

STEP 2

Flow Curves:
3% GQ in 1.5% KCl (wt/wt %)

Figure 7a
Flow Curves:
3% GQ in 1.5% KCl (wt/wt %)
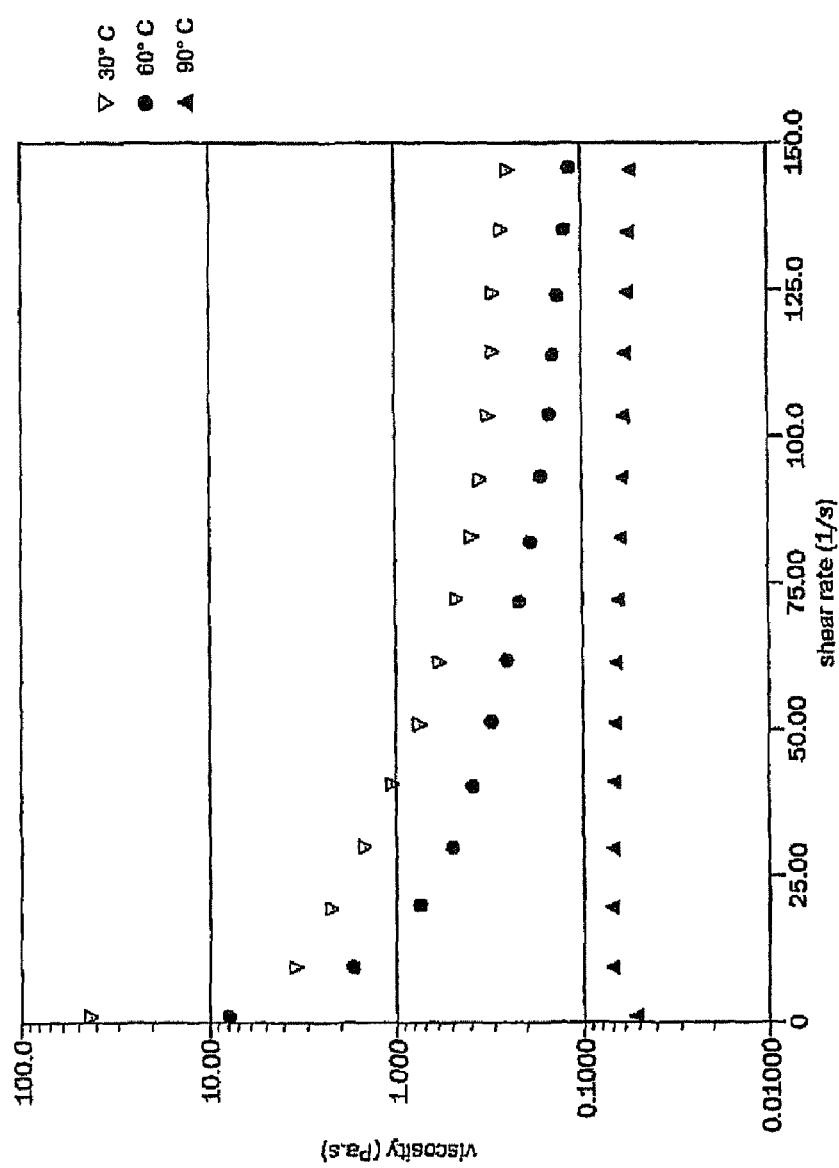
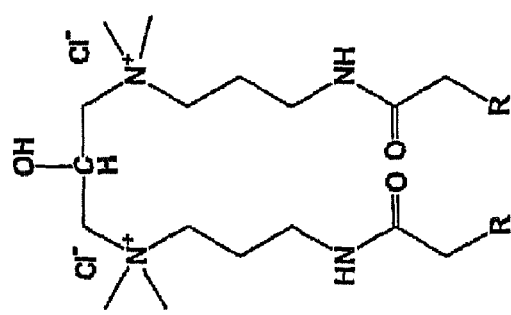
Figure 7b

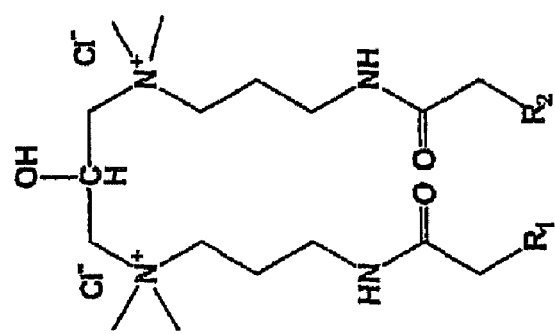
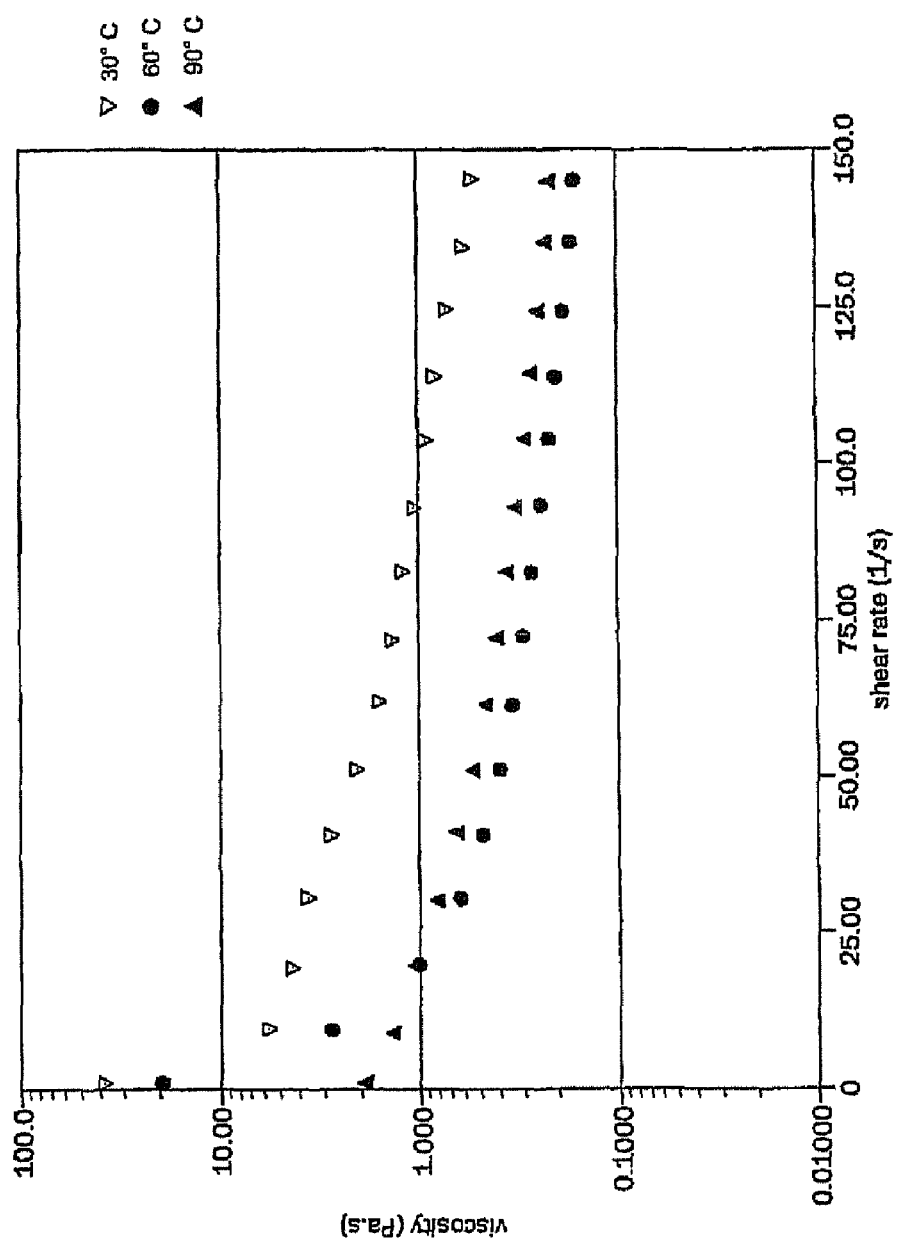
Figure 8b
Figure 8a
Flow Curves:
3% GQ in 1.5% KCl (wt/wt %)

Flow Curves:
1.25% GQ in 1.5% KCl (wt/wt %)

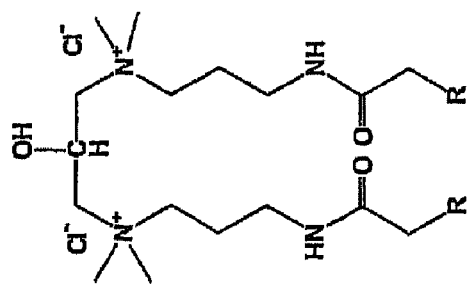
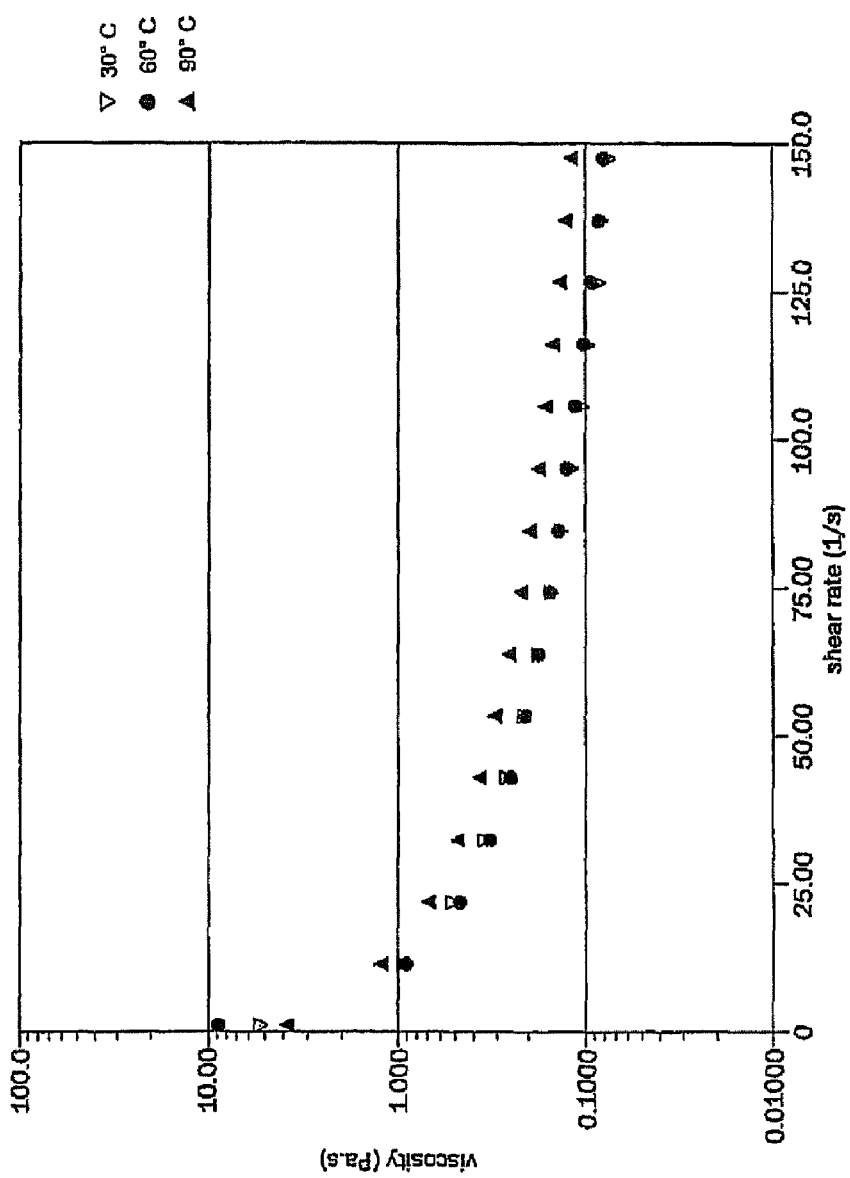
Figure 10a
Figure 10b
Flow Curves:
3% GQ in 0.5% SXS (wt/wt %)

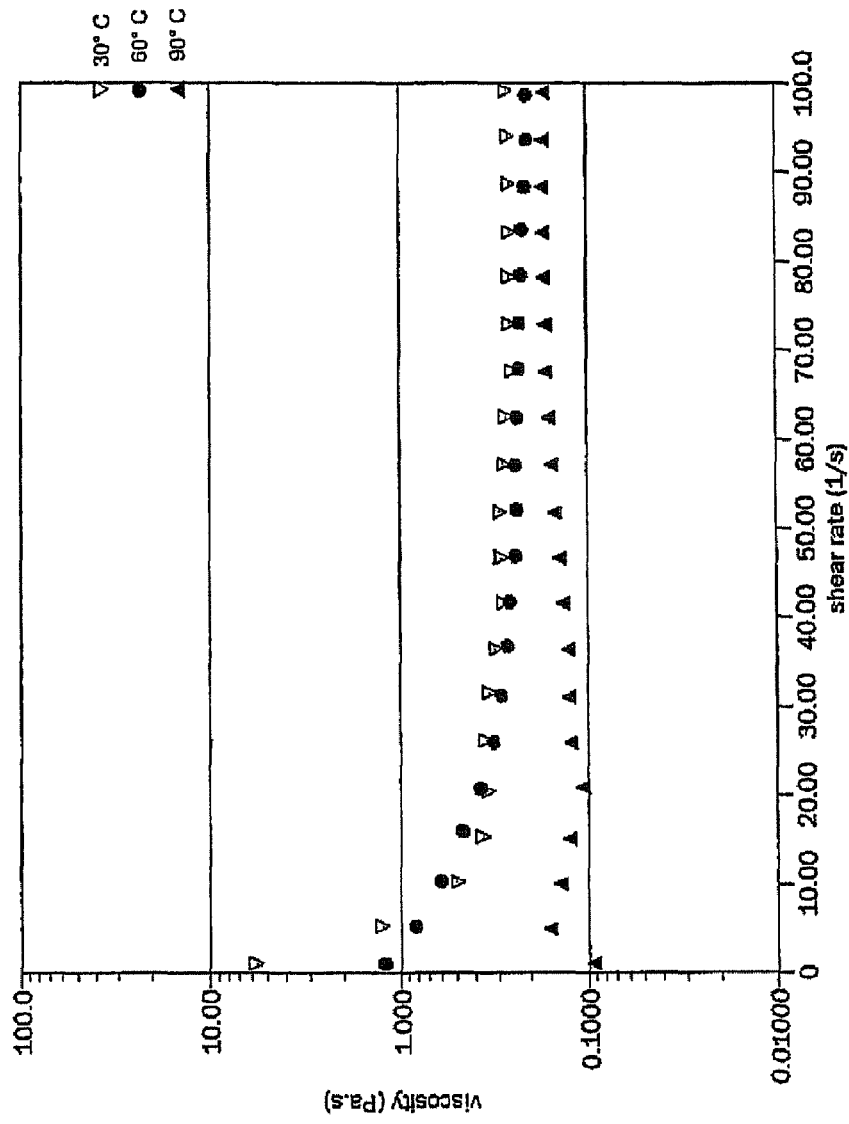

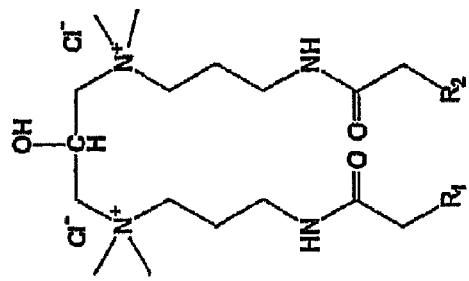
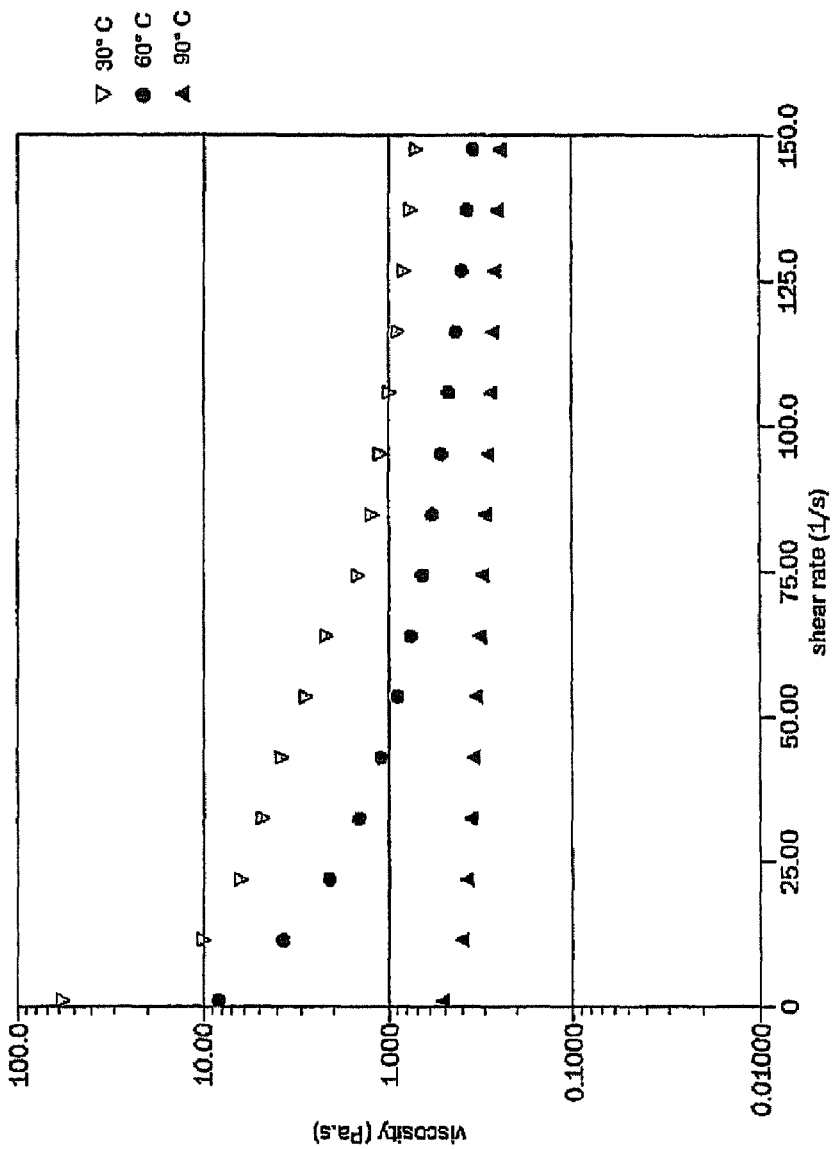
Figure 11a
Figure 11b

Flow Curves:
2.5% BQ in 25% CaBr₂ (wt/wt %)

Flow Curves:
2.75% BQ in 6% CaBr₂ (wt/wt %)

POLYCATIONIC VISCOELASTIC COMPOSITIONS

CROSS-REFERENCE TO RELATED APPLICATIONS

This application is a divisional of U.S. patent application Ser. No. 12/098,881, filed on Apr. 7, 2008, now U.S. Pat. No. 7,772,165 which application is a continuation of PCT Application No. PCT/US06/43191, filed on Nov. 7, 2006, which claims the benefit of U.S. provisional application Ser. No. 60/734,465, filed on Nov. 7, 2005. The contents of the above-identified applications are hereby incorporated by reference to provide continuity of disclosure.

FIELD OF THE INVENTION

The presently described technology generally relates to polycationic quaternary ammonium compounds and polycationic viscoelastic compositions made therewith. Polycationic viscoelastic compositions of the present technology are suitable for use in a variety of applications where viscoelasticity is a desirable characteristic. Examples of such applications include, for example, hydraulic fluids, demulsifiers, foamers, organoclays, thickeners, biocides, and oil field fluids.

One or more preferred polycationic viscoelastic compositions of the present technology impart useful rheological properties to aqueous solutions at relatively low concentrations of active ingredients (e.g., gemini quaternary compounds). Useful rheological properties provided by one or more preferred compositions of the present technology include, for example, viscoelasticity, increased viscosity, shear-thinning, and drag reduction in moving fluids.

BACKGROUND OF THE INVENTION

Some examples of bis-quaternary or polycationic quaternary ammonium compounds have been studied and reported. For example, U.S. Pat. No. 4,734,277, to Login, issued on Mar. 29, 1988, describes the preparation of certain bis-quaternary compounds by reacting tertiary amines with a suitable epoxide, such as epichlorohydrin, and further discloses that the resulting bis-quaternary ammonium compounds have utility as an additive in cosmetics applications, such as hair conditioners, skin lotions, etc.

For another example, U.S. Pub. Pat. Appl. 2004/0067855, to Hughes, et al., published on Apr. 8, 2004, discloses certain bis-quaternary or oligomeric cationic quaternary ammonium compounds useful in a viscoelastic well bore treatment fluid for controlling the viscoelasticity of that fluid.

Hydrocarbons such as oil, natural gas, etc., are obtained from a subterranean geologic formation by drilling a well that penetrates the hydrocarbon-bearing formation. This drilling outcome provides a partial flow path for the hydrocarbon, typically oil, to reach the surface. In order for oil to travel from the formation to the well bore (and ultimately to the surface), there must be a sufficiently unimpeded flow path through the rock formation (e.g., sandstone, carbonates), which generally occurs when rock pores of sufficient size and number are present.

A common impediment to oil production is "damage" to the formation, which plugs the rock pores and impedes the flow of oil. Moreover, depletion of zones nearest to the well bore causes a gradual decline in production. Generally, techniques used to increase the permeability of the formation and to provide extended conduits to the well bore are referred to as "stimulation." Aqueous gels are often used in different well stimulation processes.

For example, in a fracturing process, which is one kind of well stimulation technique, cracks or fissures (fractures) are created in subterranean formations. Gels are used in fracturing processes as the medium which transfers energy from outside the subterranean formation to the specific locations inside the subterranean formation in order to create the desired fractures. The energy to create the fractures is transferred primarily as pressure against the formation, by pumping the fracturing fluid into the well bore where it is directed to desired portions of the subterranean formation. The gels are relatively incompressible fluids, and pressure is exerted against the subterranean formation until the force is sufficient to fracture the formation. Once the fracture is created, the high viscosity of the gel is important as it flows into the newly formed cracks and fissures. As the fracturing fluid flows into the fracture, it carries proppant (e.g., small particles of sand, ceramics, or other hard material) into the fracture. Once the force from pumping the fracturing fluid is removed, the proppant remains in the fractures, which prevents the fractures from closing. The fracturing fluid is then removed from the well bore, and the well bore is prepared for recovering further amounts of hydrocarbon(s).

Older technology utilizes polysaccharide polymers to form the aqueous gels utilized as fracturing fluids. Often, the polysaccharide gels are cross-linked using additives such as titanates, zirconates or borates. Once the fracturing process is complete, these gels normally require a separate process to remove them from the well bore, which typically requires a significant amount of time and additional well treatment chemicals. Furthermore, complete removal of the polymer gel is seldom attainable, and the polymer that remains in the well bore can clog the pores of the rock formation, thus preventing hydrocarbon from flowing through and from the pores.

Non-polymeric gellants (NPGs) are more recent technological developments that provide alternatives to polysaccharide gels. NPGs are surfactants, and usually are quaternary ammonium compounds (cationic) or amphoteric compounds. Particularly desired NPGs form viscoelastic solutions (VESs) because certain properties of VESs prove useful for well stimulation processes. One such property is the ability of a VES to support proppant at lower viscosities than a polymer solution. Another useful property is the reduction of friction between the moving fluid and the surfaces contacted therewith. An especially useful feature of VES gels is that, on contact with hydrocarbons, the gels break with a resultant sharp drop in viscosity. At the lower viscosity, removal of the fracturing fluid from the well bore requires no additional well treatment chemicals, and requires less time and equipment than do polymeric gellants. NPG surfactant gels may also be broken by other means. Furthermore, unlike polysaccharide gellants, NPGs have substantially less tendency to clog the hydrocarbon-producing pores in the subterranean formation.

NPGs are also useful in other well treatment applications. For example, they can reduce the loss of fracturing fluid into subterranean formations; reduce the production of water from wells; form gels for well bore cleaning; and reduce friction between flowing solutions and solid objects.

The application of viscoelastic surfactants in both non-foamed and foamed fluids used for fracturing subterranean formations has been described in several patents, e.g., EP 0835983 B1, to Brown et al., issued Dec. 17, 2003; U.S. Pat. No. 5,258,137, to Bonekamp et al., issued on Nov. 2, 1993; U.S. Pat. No. 5,551,516, to Norman et al., issued on Sep. 3, 1996; U.S. Pat. No. 5,964,295, to Brown et al., issued on Oct. 12, 1999; and U.S. Pat. No. 5,979,557 to Card et al., issued on Jun. 16, 1999.

The use of viscoelastic surfactants for water shut off treatments and for selective acidizing is discussed in British Patent Application No. GB 2332224 A, to Jones et al., published on Jun. 16, 1999; and Chang F. F., Love T., Affeld C. J., Blevins J. B., Thomas R. L. and Fu D. K., "Case study of a novel acid diversion technique in carbonate reservoirs", Society of Petroleum Engineers, 56529, (1999).

More recent developments in this field can be found in U.S. Pub. Pat. App. No. 2004/0102330 A1, to Zhou, et al., published on May 27, 2004, which describes cleavable monomeric VES surfactants; and U.S. Pub. Pat. App. No. 2004/0067855 A1, to Hughes, et al., published on Apr. 8, 2004, which describes oligomeric anionic or cationic VES surfactants (including dimeric and trimeric forms).

Conventional cationic NPGs used in the hydrocarbon recovery field utilize alkyl amines with a single hydrophobic carbon chain. To be useful in fracturing applications, the hydrophobe chains of conventional cationic NPGs are preferably and predominantly 18 carbon atoms in length, and more preferably greater than 18. An example of one such commercially available material is ClearFRAC™, commercially available from Schlumberger-Doll Research ("Schlumberger," Ridgefield, Conn.), i.e., erucyl-N,N-di-(2-hydroxyethyl)-N-methylammonium chloride (EHMAC), which is asserted to provide performance at the highest application temperatures (up to about 250° F. (about 121° C.)) of any currently commercially available viscoelastic fracturing fluid. This product reportedly contains less than 3% hydrophobe carbon chains of 18 carbons or less. Because the intermediate used to make EHMAC must be purified to remove the components with alkyl chains of 18 carbons or less, EHMAC costs substantially more to produce than other alkyl amine cationic materials. The high cost of EHMAC limits the number of stimulation processes for which it is used on a repeated basis.

A commercially available alternative to ClearFRAC™ is AquaClear™ surfactant fracturing fluid, commercially available from BJ Services Company ("BJ Services", Huston, Tex.). It also uses a quaternary alkylamine, but is less costly because an extensively purified intermediate is not required. However, the maximum application temperature for AquaClear™ is about 170° F. (about 76.7° C.), which is substantially lower than ClearFRAC™'s 250° F. (about 121° C.).

While having some obvious advantages over polysaccharide gels, conventional NPG gels also have some disadvantages. One is the temperature limitation of conventional NPG surfactant gels. As well depth increases, well bore hole temperature usually also increases, and may frequently exceed 250° F. (about 121° C.). Currently, conventional NPG surfactant technology fails under these conditions, while polysaccharide gels continue to perform. Another disadvantage is cost, in that the material cost for polysaccharide gels is substantially lower than that for NPG surfactant gels.

Yet another disadvantage of conventional NPG surfactants is their toxicity to the environment and their poor biodegradability. Because cationic alkylamines do not breakdown readily in the environment, they tend to accumulate. Alkylamine quaternary compounds are also toxic to many life forms, so they can have a destructive impact, particularly on environments in which they accumulate. Some areas of the world have imposed regulatory restrictions on chemicals based on their being hazardous to the environment. For example, in the North Sea, chemicals such as cationic alkylamine are either restricted or banned entirely.

Thus, there is a need for gellants, in particular, viscoelastic gellants, that can provide all or most of the advantages of the conventional NPG technology, and that (1) can provide viscoelastic properties at higher temperatures (greater than 80° C. or 176° F., and preferably greater than 110° C. or 230° F.); (2) are more eco-friendly; and/or (3) are more cost effective. The presently described technology addresses these needs.

BRIEF SUMMARY OF THE INVENTION

It has been surprisingly found that polycationic quaternary ammonium compounds of the presently described technology that have at least two cationic sites connected through a linker can be used as active ingredients to form viscoelastic compositions with distinctive and useful properties.

Bis-quaternary compounds of the present technology can be symmetric or dissymmetric. For example, in one aspect, the presently described technology provides one or more viscoelastic compositions comprising water and at least one polycationic quaternary ammonium compound to control the viscoelasticity of the composition, wherein the at least one polycationic quaternary ammonium compound comprises a dissymmetric bis-quaternary compound of the following general formula:

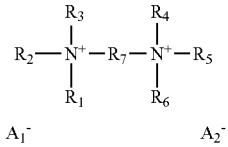

In a preferred embodiment, $R_2$, $R_3$, $R_4$, and $R_5$ are members independently selected from: (a) hydrocarbyl groups having from about 1 to about 4 carbon atoms; or (b) substituted hydrocarbyl groups having from about 1 to about 4 carbon atoms; or alternatively wherein $R_2$ and $R_3$ are members of a heterocyclic ring, and $R_4$ and $R_5$ are members of a different heterocyclic ring or are independently selected from group (a) as defined above or group (b) as defined above. Additionally, in this preferred embodiment, $R_7$ is a member selected from: hydrocarbyl groups having from about 2 to about 30 carbon atoms, or substituted hydrocarbyl groups having from about 2 to about 30 carbon atoms. Further, in this preferred embodiment, $R_1$ and $R_6$ are members independently selected from: group (a) as defined above; group (b) as defined above, or (c) hydrocarbyl groups having from about 13 to about 40 carbon atoms or substituted hydrocarbyl groups having from about 13 to about 40 carbon atoms. In this preferred embodiment, at least one of $R_1$, $R_2$, or $R_3$ is different from each of $R_4$, $R_5$ and $R_6$. Finally, $A_1^-$ and $A_2^-$ are independently selected from: (i) negatively charged inorganic ions; (ii) organic molecules with one or more negatively charged functional groups; or (iii) negatively charged functional groups which are part of $R_1$, $R_2$, $R_3$, $R_4$, $R_5$, $R_6$, or $R_7$. In particularly preferred embodiments, the viscoelastic composition provides viscoelasticity at a temperature of at least about 80° C.

It should be appreciated that hydrocarbyl or substituted hydrocarbyl groups for the presently described technology can be aliphatic, aromatic, acyclic or cyclic.

Further, the components of bis-quaternary compounds of the present technology can be derived from any suitable fatty acid source, such as animal, vegetable or hydrocarbon sources. As described herein, preferred embodiments of various components are derived from animal or vegetable fatty acid sources.

In at least one aspect, the present technology provides modified polycationic compositions in which the polycationic molecules have additional chemical functional groups. For example, in at least one embodiment, a viscoelastic composition is provided that comprises water and an effective amount of at least one polycationic quaternary ammonium compound to control the viscoelasticity of the composition, wherein the at least one polycationic quaternary ammonium compound comprises a carboxylate functional polycationic quaternary ammonium compound. Preferably, the carboxylate functional polycationic quaternary ammonium compound in such an embodiment is produced by converting at least one alkoxide nucleofuge in a quaternary ammonium compound to a carboxylate group with an acid anhydride.

Certain viscoelastic compositions of the present technology can be used in, for example, well bore treatment fluids, drilling fluids, thickeners, completion fluids, diversion fluids, and many other applications where thickened or gelled aqueous compositions are desired. For example, some embodiments of viscoelastic compositions of the present technology can be used in personal care compositions. In at least one embodiment, the present technology provides a clear viscoelastic composition comprising water and least one polycationic quaternary ammonium compound comprising a symmetric or dissymmetric bis-quaternary compound of the present technology. In one such embodiment, a clear viscoelastic composition comprises water and least one polycationic quaternary ammonium compound comprising a dissymmetric bis-quaternary compound of the following general formula:

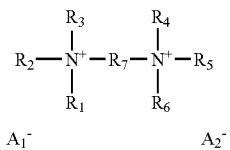

wherein $R_2$, $R_3$, $R_4$, and $R_5$ are members independently selected from: (a) hydrocarbyl groups having from about 1 to about 4 carbon atoms; or (b) substituted hydrocarbyl groups having from about 1 to about 4 carbon atoms; or alternatively wherein $R_2$ and $R_3$ are members of a heterocyclic ring, and $R_4$ and $R_5$ are members of a different heterocyclic ring or are independently selected from group (a) as defined above or group (b) as defined above; wherein $R_7$ is a member selected from hydrocarbyl groups having from about 2 to about 30 carbon atoms, or substituted hydrocarbyl groups having from about 2 to about 30 carbon atoms; wherein $R_1$ and $R_6$ are members independently selected from: group (a) as defined above; group (b) as defined above, or (c) hydrocarbyl groups having from about 13 to about 40 carbon atoms or substituted hydrocarbyl groups having from about 13 to about 40 carbon atoms; wherein at least one of $R_1$, $R_2$, or $R_3$ is different from each of $R_4$, $R_5$ and $R_6$; wherein $A_1^-$ and $A_2^-$ are independently selected from: (i) negatively charged inorganic ions; (ii) organic molecules with one or more negatively charged functional groups; or (iii) negatively charged functional groups which are part of $R_1$, $R_2$, $R_3$, $R_4$, $R_5$, $R_6$, or $R_7$.

Compared with conventional viscoelastic surfactants, one advantage of at least some embodiments of polycationic quaternary ammonium compounds (polycationic "quats") of the presently described technology is that they utilize substantially lower cost, commodity or readily available raw materials. For example, in at least some embodiments, at least one of $R_1$ or $R_6$ is derived from a carboxylic acid derived from an animal or vegetable oil.

The amount of polycationic quaternary ammonium compounds of the present technology in a viscoelastic composition should be sufficient to provide the viscoelasticity needed for the composition and application desired. For example, in some embodiments, the amount of polycationic quaternary ammonium compound is less than about 10% by weight based on the total weight of the viscoelastic composition. Current commercial systems tend to use polycationic quats in amounts of 3% to 4% by weight, and certain preferred embodiments of the present technology thus offer the advantage of requiring lower quantities of polycationic quats to achieve comparable or noticeably higher composition viscosities.

Compared with conventional VES surfactants, one or more preferred polycationic quats of the present technology also tend to have higher viscosities at higher temperatures. Preferably the viscoelasticity of such compositions can be maintained at a temperature of at least about 80° C., alternatively at greater than about 80° C., such as at temperatures of about 85° C., about 90° C., about 95° C., or higher. More preferably, the viscoelasticity of such compositions can be maintained at a temperature of at least about 100° C., alternatively at greater than about 100° C. Most preferably the viscoelasticity of such compositions can be maintained at a temperature of at least about 110° C., alternatively at greater than about 110° C. Therefore, the useful working temperatures of well bore treatment fluids based on the present technology, for example, can be increased as compared to the useful working temperatures of well bore treatment fluids based upon conventional technology.

At least some embodiments of viscoelastic gels of the present technology can be prepared by using methods in current commercial practice (e.g., combining polycationic compounds of the present technology with potassium chloride (KCl) or sodium xylene sulfonate (SXS)), or by using the active ingredient in water without additives in some cases.

Further, one or more preferred embodiments of polycationic quats of the present technology are more susceptible than conventional alkylamine cationic compounds to natural chemical degradation processes such as hydrolysis, so they degrade in the environment faster than do alkylamine cationic compounds. Therefore, some embodiments of preferred chemical compounds of the present technology are expected to be less environmentally harmful and accumulate less in the environment than do alkylamine cationics, for example.

BRIEF DESCRIPTION OF SEVERAL VIEWS OF THE DRAWINGS

FIG. 2 also shows that the linker in the gemini quat can be subsequently modified to produce a modified gemini quat.

FIG. 7a shows flow curves of a VES containing 3% gemini (cetyl/oleyl)amidopropyl-dimethylammonium di-chloride ((16APDMA/18:1APDMA)-3-(OH)-(16APDMA/18:1 APDMA)) in 1.5% KCl (wt/wt %).

FIG. 7b shows a molecule structure of (16APDMA/18:1APDMA)-3-(OH)-(16APDMA/18:1 APDMA).

FIG. 8a shows flow curves of a VES containing 3% dissymmetric gemini oleamidopropyldimethylammonium-stearamidopropyl-dimethylammonium di-chloride ((18:1APDMA)-3-(OH)-18-APDMA) in 1.5% KCl (wt/wt %)

FIG. 8b shows a molecule structure of (18:1APDMA)-3-(OH)-18-APDMA.

FIG. 10a shows flow curves of a VES containing 3% gemini high erucic rapeseed amidopropyldimethylammonium di-chloride (HERAPDMA-3-(OH)-HERAPDMA or HERAPDMA GQ) in 0.5% SXS (wt/wt %).

FIG. 10b shows a molecule structure of HERAPDMA GQ.

FIG. 10c shows flow curves of a VES containing 2% HERAPDMA GQ in 1.5% KCl (wt/wt %).

FIG. 11a shows flow curves of a VES containing 3% dissymmetric gemini behenamidopropyldimethylammonium-high erucic rapeseed amidopropyldimethyl-ammonium di-chloride (22APDMA-3-(OH)-HERAPDMA).

FIG. 11b shows a molecule structure of 22APDMA-3-(OH)-HERAPDMA.

DETAILED DESCRIPTION OF THE INVENTION

Definitions and Conventions

Figure 1:
FIG. 1 is a schematic representation of at least one bis-quaternary ammonium compound of the present technology consisting of one linker fragment and two cationic fragments, wherein the two cationic fragments are either the same or different and randomly joined.

As used herein, the term "acyclic" pertains to aliphatic compounds and/or groups which are linear or branched, but not cyclic (also known as "open-chain" groups).

As used herein, the term "alicyclic" pertains to compounds and/or groups which have one ring, or two or more rings (e.g., spiro, fused, bridged), wherein said ring(s) are not aromatic.

As used herein, the term "aromatic" pertains to unsaturated compounds with at least one closed ring of at least 5 atoms, with all of the ring atoms being co-planar or almost co-planar and covalently linked, and with all of the ring atoms being part of a mesomeric system. As used herein, when the "aromatic" substituent is monocyclic, it preferably contains 5 or 6 ring atoms, and when the "aromatic" substituent is polycyclic, it preferably contains 9 or 10 ring atoms contained in fused rings.

As used herein, the terms "carbo," "carbyl," "hydrocarbon" and "hydrocarbyl", pertain to compounds and/or groups which have only carbon and hydrogen atoms.

As used herein, the term "cyclic" pertains to compounds and/or groups which have one ring, or two or more rings (e.g., spiro, fused, bridged). Compounds with one ring may be referred to as "monocyclic" or "mononuclear" whereas compounds with two or more rings may be referred to as "polycyclic" or "polynuclear."

As used herein, the term "heterocyclic" pertains to cyclic compounds and/or groups which have one heterocyclic ring, or two or more heterocyclic rings (e.g., spiro, fused, bridged), wherein said ring(s) may be alicyclic or aromatic.

As used herein, the term "heterocyclic ring" pertains to a closed ring of from about 3 to about 10 covalently linked atoms, more preferably about 3 to about 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

As used herein, the term "hydrophobe" refers to hydrophobic segments of atoms in molecules that include a straight or branched hydrocarbon chain of five or more carbon atoms.

As used herein, the term "polycationic" pertains to molecules that have two or more atoms which have a positive electrical charge, preferably at all pHs.

As used herein, the term "ring" pertains to a closed ring of from about 3 to about 10 covalently linked atoms, more preferably about 5 to about 7 covalently linked atoms.

As used herein, the term "saturated" pertains to compounds and/or groups which do not have any carbon-carbon double bonds or carbon-carbon triple bonds.

As used herein, a "substitution reaction" is defined according to the IUPAC *Compendium of Chemical Terminology* as "a reaction, elementary or stepwise, in which one atom or group in a molecular entity is replaced by another atom or group."

As used herein, the term "unsaturated" pertains to compounds and/or groups which have at least one carbon-carbon double bond or carbon-carbon triple bond.

As used herein, "viscoelastic" composition (e.g., solution, fluid, or gel), means the elastic (or storage) modulus G' of the composition is equal to or greater than the loss modulus G" as measured using an oscillatory shear rheometer (such as a Bohlin CVO 50 or TA Instruments AR2000) at least one frequency between 0.0001 Hz and 1 Hz and at 20° C. The measurement of these moduli is further described in "An Introduction to Rheology," by H. A. Barnes, J. F. Hutton, and K. Walters, Elsevier, Amsterdam (1997). The disclosure of such measurements in "An Introduction to Rheology" is hereby incorporated by reference.

DESCRIPTION OF THE INVENTION

While the presently described technology is described herein in connection with one or more preferred embodiments, it should be understood that it is not limited to those embodiments. On the contrary, the presently described technology includes all alternatives, modifications, and equivalents to those embodiments as may be included within the spirit and scope of the appended claims.

In a first aspect, the presently described technology relates to viscoelastic compositions of polycationic quats that have at least two cationic sites. The cationic sites of polycationic quats of the present technology are quaternary ammonium chemical functional groups. The molecules of the polycationic quats can also have other chemical functional groups. Additionally, the molecules of the polycationic quats can be symmetric or dissymmetric. Each cationic functional group is connected to another cationic functional group by a "linker," and an example of such an arrangement is illustrated by FIG. 1.

In most cases, each linker is derived from a molecule which is capable of undergoing two or more substitution reactions. The linker may be the substrate of a molecule in a substitution reaction of the molecule with an amine, though the linker may itself have amine functional groups.

In accordance with at least one embodiment of the present technology, in the substitution reaction, a nitrogen atom of an amine becomes bonded to a carbon atom of the linker precursor molecule. In this substitution reaction, the amine nitrogen that forms a bond with the substrate carbon atom may be referred to as the "nucleophile," while the atom or group that becomes detached from an atom of the substrate is called the "leaving group." However, it is not necessary for the leaving group to become detached from the substrate completely. It is only needed to become detached from the carbon atom which becomes attached to the amine nitrogen for a sufficient number of molecules.

A person of ordinary skill in the art will understand that an amine nitrogen may be capable of undergoing more than one such substitution reaction. In general, the number of times an amine nitrogen can undergo a substitution reaction is equal to the number of hydrogen atoms bonded to the nitrogen of the free amine plus one. For purposes of discussion in this disclosure, the number of times an amine nitrogen may participate in a substitution reaction is referred to as its theoretical functionality ("F") (which is different from chemical functional groups). Amines that can themselves become linkers have theoretical functionality of about 2 or more. With mixtures of amines with different theoretical functionality, an expression of "average functionality" is useful. Average functionality is simply the equivalents of a reactive group divided by the moles of reactive molecules:

Average Functionality=(Total Equivalents of Theoretical Functionalities)/(Total Moles).

Thus, an equal molar mixture of dimethylamine, with a functionality of 2, and trimethylamine, with a functionality of 1, has an average functionality of 1.5. These concepts are important for insights into such phenomena as chain branching and chain termination in cases where non-quaternary amines are linkers, or in higher polycationic quats, where polycationic quats may become multi-chained and highly networked.

When the leaving group is negatively charged, it can be called a nucleofuge. A nucleofuge may remain in the viscoelastic composition of the present technology as the negative counter ion (anion) to a quaternary ammonium cation. A nucleofuge may also be converted chemically to another anion, or it may be exchanged with anions from an externally supplied source. A net electrical charge of zero is maintained by the presence of counter ions (anions) in a polycationic composition. The counter ions to the quaternary ammonium cations of the present technology can be one or more negatively charged inorganic atoms or functional groups of atoms, and can be from one or more negatively charged organic molecules.

A linker in the polycationic quat molecule may be hydrophilic, hydrophobic or essentially neither. The presence of both electrically charged and/or polar atoms (which are hydrophilic) and hydrophobe(s) in the linker promotes the surface activity of the molecule. Preferred linkers are hydrophilic, in that the have atoms capable of forming hydrogen bonds with water or other polar molecules.

Viscoelastic compositions of the present technology, such as viscoelastic solutions (VESs) or gels, can be prepared by combining polycationic quats of the present technology with water, and optionally with additional additives, such as inorganic salts, anionic hydrotropes or surfactants, or other useful organic compounds (such as carboxylic or polycarboxylic acids). The order of mixing is typically not particularly important to achieving a viscoelastic composition.

Typically, viscoelastic solutions and gels are prepared through dissolution of gellant compounds in base solutions. Any suitable mechanical means for obtaining a homogeneous solution is acceptable. Base solutions normally provide the bulk of the viscoelastic solutions or gels, typically up to about 90% or greater by weight. Base solutions can comprise water. Base solutions can also contain salt(s), and can have up to about 65 wt % salt. Metal (or ammonium) halide salts are used most commonly, but other inorganic mineral acid salts may also be used. Alternatively, the base solution may be a polar organic compound dissolved in water. Non-exhaustive examples of such compounds include salicylic acid (or salts thereof), phthalic acids (or salts thereof), or organic sulfonic acids (or salts thereof).

When preparing viscoelastic gels, air bubbles are frequently trapped in the gels and should be removed before accurate viscosity measurements can be made. Centrifugation, ultrasonication in warm water baths, and heating in ovens at between about 70° C. and about 80° C. overnight can be used to induce bubble-free gels.

In at least some aspects, polycationic quats of the present technology can be provided in the form of a concentrated solution in an organic solvent (e.g., alcohols, ketones, or glycol ethers) before being mixed with water to make an aqueous viscoelastic composition for a specific application. For example, when used as a gelling agent, the polycationic quats of the present technology can first be dissolved in an alcohol, such as isopropyl alcohol, preferably with some water, to make a concentrated solution, in which the concentration of the active ingredient can be made as high as possible while maintaining desirable handling properties, such as fluidity. Suitable concentrations of the polycationic compound can range from about 20% to about 60%, or higher, by weight. The concentrated polycationic compound solution can then be added to water, or a water solution of salt, organic acids, etc., with mixing to make a viscoelastic composition (such as a solution or gel) containing an effective amount of the polycationic quats of the present technology suitable for use in one or more oil field applications.

Particularly when used as well bore fluids, viscoelastic compositions of the presently described technology are generally thickened aqueous compositions, and preferably comprise less than about 10 wt % of polycationic quats of the present technology. For example, in some embodiments, viscoelastic compositions can comprise from about 5 wt % to about 8 wt % of polycationic quats of the present technology. More specifically, preferred viscoelastic compositions of the present technology can comprise any amount of polycationic quats of the present technology less than about 10 wt %, such as about 8 wt %, about 6 wt %, about 5 wt %, about 4 wt %, about 3 wt %, about 2.5 wt %, about 2 wt %, about 1.5 wt %, or about 1 wt %. In some embodiments, viscoelastic compositions of the present technology comprise less than about 1 wt % polycationic quats, such as about 0.75% wt %, about 0.5 wt %, about 0.25 wt %, or about 0.1 wt %. Some viscoelastic compositions of the present technology comprise from about 0.1 wt % to about 5 wt %, from about 0.25 wt % to about 4 wt %, from about 0.25 wt % to about 3 wt %, or from about 1.0 wt % to about 2.0 wt % of polycationic quats of the present technology.

Additives, such as inorganic salts (electrolytes), organic acids, salts of organic acids, poly acids, salts of poly acids, diacids, salts of diacids, anionic surfactants, anionic hydrotropes, poly-anionic polymers, or combinations thereof, can be added to viscoelastic compositions of the present technology depending on the demands of the particular application. Some additives can impart higher viscosities to viscoelastic solutions at elevated temperatures, as compared to the same systems without these additives. However, additives are not required in all applications and compositions of the present technology.

Inorganic salts that can be useful as additives in viscoelastic compositions include, for example, halide salts (predominantly bromides and chlorides) of alkali metals (such as sodium, potassium, cesium) or alkaline earth metals (such as calcium and magnesium). Some preferred inorganic salts for use in viscoelastic solutions of the present technology include, but are not limited to, sodium chloride (NaCl), potassium chloride (KCl), ammonium chloride ($NH_4Cl$), calcium chloride ($CaCl_2$), sodium bromide (NaBr), calcium bromide ($CaBr_2$), and zinc bromide ($ZnBr_2$), potassium formate (KHCOO), cesium chloride (CsCl), cesium bromide (CsBr), or combinations thereof.

Examples of other additives can include organic acids (e.g., carboxylic or sulfonic acid), diacids, polyacids, and salts of these acids. Organic molecules bearing negative charge(s), typically derived from organic acids can be used to provide organic counter ions. For example, ortho-phthalate salts can be prepared by mixing o-phthalic anhydride in water with bases, such as alkali metal hydroxides (NaOH or KOH) or tertiary amines (e.g. triethylamine). The organic acids, or their salts, may also be present as pendant groups on polymer chains. Such polymers are referred to herein as poly-anionic polymers.

Hydrotropes are also useful in certain circumstances. Examples of suitable hydrotropes can include sodium xylene sulfonate (SXS), sodium cumene sulfonate (SCS), and ammonium xylene sulfonate (AXS). Anionic surfactants may also provide desirable properties in conjunction with certain polycationic quats of the present technology used as active ingredients.

In some preferred embodiments of the present technology for use as viscoelastic well bore treatment fluids in oil fields, such fluids contain viscoelastic compositions as described above, such as compositions of water and at least one polycationic quaternary ammonium compound of the present technology to control the viscoelasticity of the composition. In some such embodiments, well bore treatment fluids of the present technology further comprise a proppant. Proppants suitable for use with the present technology can be, but are not limited to, small particles of sand, ceramics, or other hard materials.

Polycationic quats of the present technology tend to have higher viscosities at higher temperatures as compared to conventional NPGs. In one or more preferred embodiments, the polycationic quats of the present technology provide viscoelasticity such that the viscoelastic compositions of the present technology maintain viscoelasticity at a temperature of at least about 80° C., or greater than about 80° C., such as at temperatures of about 85° C., 90° C., 95° C., or higher. More preferably, the viscoelasticity of viscoelastic solutions of the present technology can be maintained at a temperature of at least about 100° C., or greater than about 100° C. Most preferably, the viscoelasticity of viscoelastic solutions of the present technology can be maintained at a temperature of at least about 110° C., or greater than about 110° C.

Random Bis-Quaternary Ammonium Compounds

Bis-quaternary ammonium compound ("bis-quat") molecules that have two quaternary ammonium atoms and two or more hydrophobes are commonly called "gemini" quaternary compounds, and may be referred to as GQs hereafter.

In accordance with some embodiments, the presently described technology provides viscoelastic compositions containing at least one GQ resulting from random substitution reactions. Such a viscoelastic composition can be called a "random GQ" composition. In the substitution process, the amine nitrogen atoms are quaternized and become cationic.

The following formula illustrates a general structure of a bis-quat molecule used in the random bis-quat compositions of this embodiment:

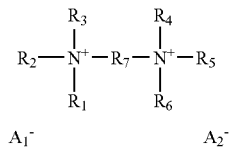

In some embodiments of bis-quat molecules of the present technology having this general structure, $R_2$, $R_3$, $R_4$, and $R_5$ can be members independently selected from (a) hydrocarbyl groups having from about 1 to about 4 carbon atoms, or (b) substituted hydrocarbyl groups having from about 1 to about 4 carbon atoms. Alternatively, $R_2$ and $R_3$ can be members of a heterocyclic ring, preferably a heterocyclic ring containing 5 or 6 carbon atoms. In such embodiments, $R_4$ and $R_5$ can be members of a different heterocyclic ring, or can be independently selected from group (a) as defined above or group (b) as defined above. When $R_4$ and $R_5$ are members of a different heterocyclic ring, that ring preferably contains 5 or 6 carbon atoms.

Additionally, in some embodiments of such bis-quat molecules of the present technology, $R_1$ and $R_6$ can be members independently selected from group (a) as defined above, group (b) as defined above, or (c) hydrocarbyl groups having from about 13 to about 40 carbon atoms or substituted hydrocarbyl groups having from about 13 to about 40 carbon atoms. In some such embodiments, the hydrocarbyl groups or substituted hydrocarbyl groups of group (c) can comprise carboxamides, carboximides, polycarboxamides, polycarboximides, carboxamidines, carboximidines, carboxylic esters, polycarboxylic esters, carboxylic acids, polycarboxylic acids, carboxylates, polycarboxylates, or combinations thereof.

In some particularly preferred embodiments, at least one of $R_1$ or $R_6$ is a member of group (c), and in some such embodiments, can further comprise a cyclo hydrocarbyl ring or a heterocyclic ring. In some embodiments, $R_1$ and $R_6$ are both chosen from group (c), while in others, only $R_1$ or $R_6$ is chosen from group (c). In at least one embodiment, $R_1$ is selected from group (c) and $R_6$ is selected from group (a) or group (b). In at last one embodiment, each of $R_4$, $R_5$, and $R_6$ is a hydrocarbyl group having from about 1 to about 4 carbon atoms or a substituted hydrocarbyl group having from about 1 to about 4 carbon atoms. In some preferred embodiments, at least one of $R_1$ or $R_6$ is derived from a carboxylic acid having from about 13 to about 40 carbon atoms, and more preferably from about 16 to about 22 carbon atoms. In some particularly preferred embodiments, the carboxylic acid is derived from an animal or vegetable oil.

When at least one of $R_1$, $R_2$, or $R_3$ and at least one of $R_4$, $R_5$ or $R_6$ are hydrophobes, the bis-quat is a gemini-quat (GQ).

The hydrocarbyl groups of groups (a), (b) and (c) can be arranged in any chemically rational combination, including aliphatic, aromatic, acyclic, or cyclic.

In embodiments of the present technology where any of $R_1$ to $R_6$ are selected from group (b), the substituted hydrocarbyl groups of group (b) can have one or more substituents selected from hydroxyl (—OH), alkoxy, aryloxy, carbonate ester, carbamate, sulfonate, phosphinate, phosphite, phosphate, phosphonate, or combinations thereof. In some such embodiments, the alkoxy or aryloxy substituents have the general formula —OR, where R is a hydrocarbyl group having from about 1 to about 4 carbon atoms.

In actual production, amines from which the quaternary ammonium sites can be formed are sometimes themselves mixtures in which the R substituents on each amine molecule can be similar, but not identical. For example, amines derived from vegetable oil fatty acids are normally mixtures. Each of the R substituents in the amines in these mixtures conforms to the above descriptions for $R_1$-$R_6$. These amine mixtures may be very complex. The theoretical number of possible combinations of amine pairs grows very rapidly as the number of kinds of amines exceeds about three, and becomes very large as the number of kinds of different amines exceeds about five. The actual product distribution function for the possible combinations is a statistical mixture which reflects the populations of the various amine components, but also reflects the relative reactivities of the different components. In at least one random GQ composition of the presently described technology, each GQ molecule is formed by a pair of amine molecules, the same kind or different, randomly met. While not strictly accurate, such a composition is called random for the purposes of this disclosure.

In the formula provided above for a general structure of a bis-quat molecule of the present technology, $R_7$ can be a member selected from hydrocarbyl groups having from about 2 to about 30 carbon atoms, or substituted hydrocarbyl groups having from about 2 to about 30 carbon atoms. For example, in some embodiments of the present technology, $R_7$ comprises hydrocarbyl groups having from about 3 to about 8 carbon atoms or substituted hydrocarbyl groups having from about 3 to about 8 carbon atoms. In preferred embodiments of this type, $R_7$ has a linear configuration. As another example, in some embodiments of the present technology, $R_7$ comprises hydrocarbyl groups having from about 9 to about 21 carbon atoms or substituted hydrocarbyl groups having from about 9 to about 21 carbon atoms. In preferred embodiments of this type, $R_7$ has a configuration comprising a ring structure.

In embodiments of the present technology where any of $R_7$ is a substituted hydrocarbyl group, the hydrocarbyl group can have one or more substituents selected from hydroxyl, alkoxy, aryloxy, ester carbonate, carbamate, sulfonic acid, sulfonate, phosphinic acid, phosphinate, phosphorous acid, phosphite, phosphoric acid, phosphate, phosphonate or combinations thereof. In some such embodiments, the alkoxy or aryloxy substituents have the general formula —OR, where R is a hydrocarbyl group having from about 1 to about 4 carbon atoms.

There are several characteristic that can be preferred for $R_7$ as used in the present technology. For example, in at least some particularly preferred embodiments, $R_7$ is hydrophilic. As another example, in at least some embodiments, $R_7$ is a substituted hydrocarbyl group that is not a hydroxyalkylene.

In various embodiments of the present technology, $R_7$ can be derived from various sources. For example $R_7$ can be derived from a di-sulfonic acid ester of a primary diol, a secondary diol, a derivative thereof, or a combination thereof. As another example, $R_7$ can be derived from an epihalohydrin. Further, $R_7$ can be derived from a bis-glycidyl ether. In at least some embodiments, $R_7$ can be derived from a di-haloalkyl hydrocarbon containing from about 2 to about 12 carbon atoms in which the two halogen atoms are attached to different primary or secondary saturated carbon atoms. In some such embodiments, the di-haloalkyl hydrocarbon can be substituted with one or more additional hydroxy, alkoxy, or aryloxy substituents, and preferably the additional substituents are not attached to one of the halogen-bearing carbon atoms. In some preferred embodiments, the di-haloalkyl hydrocarbon is selected from dichloroethane, 1,3-dichloro-2-propanol, 1,4-dibromobutane, di-(chloromethyl)benzenes, or derivatives thereof.

The anion groups $A_1$ and $A_2$ in the above formula are selected independently and can be:
1) negatively charged inorganic ions;
2) organic molecules with negatively charged functional group(s), which can be, but are not limited to, carboxylate, sulfonate or phosphate; or
3) negatively charged functional group(s) which are part of $R_1$, $R_2$, $R_3$, $R_4$, $R_5$, $R_6$ or $R_7$, which can be, but are not limited to, carboxylate, sulfonate or phosphate.

In accordance with at least some embodiments of the presently described technology, at least a portion of the hydrophobes in the GQ molecule, preferably at least a portion of the hydrophobes in $R_1$-$R_6$ of the above formula is derived from a carboxylic acid. In at least one preferred embodiment, at least one of $R_1$ or $R_6$ is derived from a carboxylic acid. Carboxylic acids suitable for use with the present technology preferably have from about 13 to about 40 carbon atoms, and more preferably have from about 16 to about 22 carbon atoms.

In at least one preferred embodiment, the carboxylic acid is derived from a fatty acid, such as an animal or vegetable oil. Carboxylic acids derived from fatty acids typically contain from about 8 to about 24 carbon atoms.

Carboxylic acids (and their derivatives, including but not limited to esters, carboxamides, carboxamidines, anhydrides, acyl chlorides and nitriles) may also be derived from other sources. Carboxylic acids from other sources offer a wider variety of structures than do those found in common fatty acids (mostly linear chains), such as cyclic, aromatic, and polyfunctional compounds. Non-fatty acid derived carboxylic acids may be used with the present technology when their structural features impart useful properties to the viscoelastic compositions.

Preferably, at least one hydrophobe is covalently bonded to a substituent on the cationic nitrogen atom through either an ester, carboxamide, or carboxamidine functional group. Hydrophobes may also be bonded to the linker fragments of the GQ molecules through ester, carboxamide, or carboxamidine functional groups. Not being bound by any theory, it is believed that surfactants in which the hydrophobes are attached through these functional groups are biodegraded more easily than those in which the hydrophobes are attached as hydrocarbyl functional groups.

One readily accessible method for preparing GQs is by substitution reactions between m moles of a substrate and 2 m moles of a tertiary amine (having a theoretical functionality of 1), where "m" is a number used herein to illustrate the ratio of moles of substrate to moles of tertiary amine, and where the substrate has 2 m equivalents of functional groups (leaving groups) that may become a nucleofuge in substitution reactions. The net theoretical functionality of the product is zero, since the 2 m moles of tertiary amines react at the 2 m equivalents of sites with leaving groups. The formation of a fourth bond to the amine nitrogen quaternizes the tertiary amine, and thus generates a cationic site.

Any molecule that has two suitable leaving groups can serve as a substrate to form the linker fragment in a GQ molecule. Preferred substrates are those in which the linker derived from the substrate separates the two cationic nitrogen atoms by from about 2 to about 12 atoms. Suitable substrates may contain other functional groups, such as hydroxyl groups, so long as they do not block the reaction between the amine and the substrate. Functional groups may also become attached to the linker fragment by additional chemical reactions subsequent to the quaternization reactions.

Figure 2:
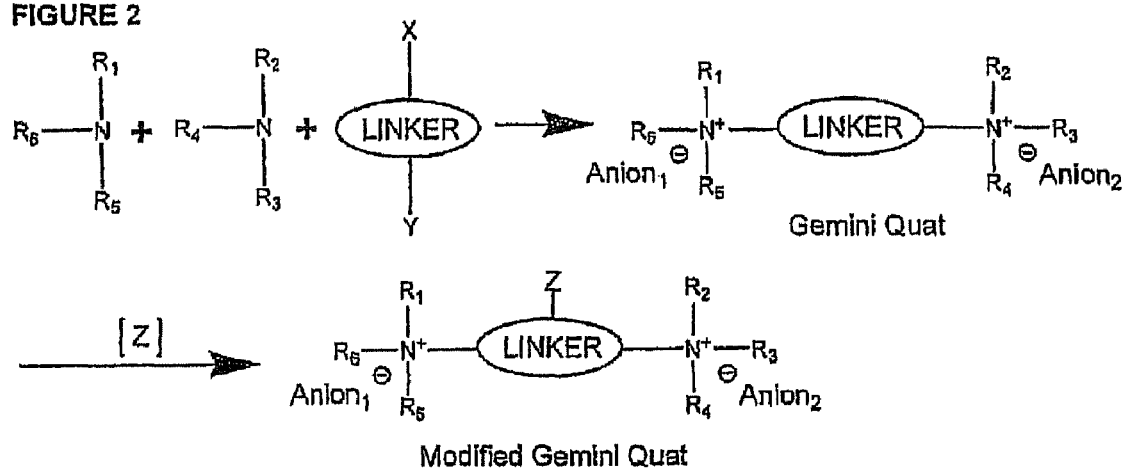
FIG. 2 is a schematic representation of at least one method of making a random gemini quat from two tertiary amines and a substrate to provide the linker.

FIG. 2 illustrates such a method. In FIG. 2, the substrate molecule has two leaving groups, X and Y, and provides two sites that can react with two amine molecules. As nucleofuges in the substitution reaction, one or both of X and Y may become $Anion_1$ ($A_1$) or $Anion_2$ ($A_2$) for the resulting GQ molecule, but not necessarily. X and Y may themselves react further after the initial substitution reactions. For example, an alkoxide nucleofuge may be converted to a carboxylate anion by reaction with an acid anhydride. FIG. 2 also shows that the resulting GQ can be modified through a subsequent reaction with [Z], which contains a functional group Z that can be bonded to the GQ, to make the modified GQ.

Examples of readily accessible substrates that may form the linker fragments through substitution reactions include, but are not limited to:
  di-haloalkyl hydrocarbons (cyclic or acyclic, aliphatic or aromatic) containing from about 2 to about 18 carbon atoms in which the two halogen atoms are attached to different primary or secondary saturated carbon atoms;
  substituted di-haloalkyl hydrocarbons (cyclic or acyclic, aliphatic or aromatic) containing from about 2 to about 18 carbon atoms in which the two halogen atoms are attached to different primary or secondary saturated carbon atoms, and in which the hydrocarbon is additionally substituted with hydroxyl (—OH); or, alkoxy and aryloxy (—OR, where R is a hydrocarbyl group having from about 1 to about 24 carbon atoms), so long as the additional substituents are not attached to one of the halogen-bearing carbon atoms;
  di-sulfonic acid esters of primary diols, secondary diols, or a combination thereof;
  epihalohydrins, or
  bis-glycidyl ethers Solvents are not necessary to prepare random GQ compositions of the presently described technology. However, random GQ compositions are preferably prepared in solvents to aid in processing and handling. Examples of solvents that can be used in the present technology include, for example, methanol, ethanol, 2-propanol, 1-propanol, 2-butanone, acetone, glycol ethers and water. In general, organic solvents with at least partial water solubility are suitable so long as they do not interfere with the chemical reactions involved in making the bis-quats or GQs. Many of the bis-quats solidify when being cooled to around room temperature, so solvents are usually preferred to facilitate handling.

Generally, when making random GQs, the amine (preferably a tertiary amidoamine) or amine mixture can be dissolved in a water compatible solvent. Water can be used as a co-solvent at levels from about 1% to about 99% by weight of the solvent composition.

Then, if an epihalohydrin substrate is used, acid can be added slowly to the solution in sufficient quantity to react with half of the tertiary amine equivalents. Once partial neutralization of the amine is completed, the substrate (e.g., epichlorohydrin) can be added to the solution slowly, typically over a period of from approximately 15 minutes to about 2 hours. The temperature during the addition of the substrate is preferably from about 25° C. to about 100° C., and more preferably from about 40° C. to about 70° C. The total charge of substrate is preferably from about 0.5 to about 0.6 moles per mole of tertiary amine. Preferably, a slight excess of the substrate, for example about 0.52 moles per mole of tertiary amine, is used to achieve sufficient quaternization such that low levels of free amine and amine salt are present in the final product.

After the substrate charge is complete, the process is continued until reaction of the substrate is complete. Reaction degree of completion may be determined by titration methods, for example by titration of residual free amine and amine salt levels, and by titration for halide content by silver nitrate methods. If necessary, additional substrate is charged to reduce levels of free amine and amine salt to acceptably low levels. Acceptably low levels are preferably such that at least about 90% of the total initial tertiary amine equivalents charged are converted to quaternary ammonium compounds (about 90% molar conversion). Once the reaction is complete, properties such as actives concentration and pH are adjusted (if desired) through the addition of additional solvents (for actives) and acids or bases (for pH adjustment).

Some bis-quats of the present technology can be used as the active ingredients in gellant compositions. Addition of undiluted solid gellant compositions to water frequently causes the solids to become coated with gel, and dissolution becomes difficult and may require additional heating, mixing and time. Formulation of the bis-quats or GQs of the present technology with organic solvents, or mixtures of organic solvents and water is preferred, because it provides liquid compositions that dissolve efficiently when added to a solution to be gelled or thickened. In instances where minimal organic solvents are desired, such as in high actives solid gellants, mechanical dissolution techniques, such as high-shear mixers, can be used to prepare gellant solutions.

The following specific reaction schemes further demonstrate methods for preparing random bis-quaternary compounds of the present technology.

Reaction Scheme 1:
In this scheme, the linker is derived from 1,2-dichloroethane. The tertiary amine is the stearamidopropyldimethylamine (SAPDMA) derived from stearic acid and 3-dimethylaminopropyl-1-amine. The chlorine atoms are nucleofuges, which become the negative counter ions (chloride) that maintain a net electrical charge of zero (charge balance). The product is a gemini stearamidopropyl gemini quat.

SCHEME 1

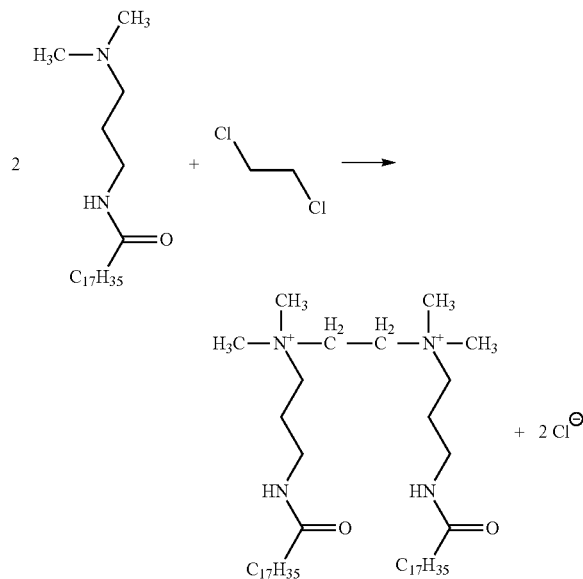

A common practice in the literature regarding gemini surfactants is to use a condensed notation to describe both the hydrophobe and the linker (also referred to as "spacer"). In general, the notation used is m-n-m, where m is the length of the hydrophobe carbon chain in the alkylamine, and n is the number of carbon atoms in the linker. Modifications to this notation are used in this disclosure to describe polycationic quats. Some designation is required to note that the hydrophobes on the bis-quats in Scheme 1 are not from alkylamines, but instead they are from amidopropyldimethylamines (APDMA). The notation used hereafter for this type of GQ is 18APDMA-2-18APDMA. This notation example specifies that both hydrophobes have 18 carbon atoms which are part of an amidopropyldimethylamines, and that the linker is a 2 carbon atom chain (ethylene).

Reaction Scheme 2:

In this scheme, epichlorohydrin is used to form the linker. One mole of acid, hydrochloric acid reacts with one mole of the tertiary amine. The epichlorohydrin reacts with the amine hydrochloride salt (through the oxirane functional group) and the free tertiary amine (through the chloromethyl group) to form the GQ. The GQ in this case may be represented by the notation 18APDMA-3(OH)-18APDMA. The linker in this case has 3 carbon atoms, but also includes a hydroxyl group, which is indicated by the (OH). As in Scheme 1, the negative counter ions are chloride.

SCHEME 2

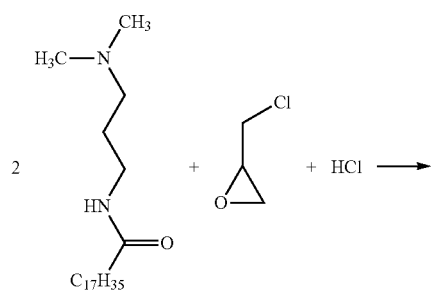

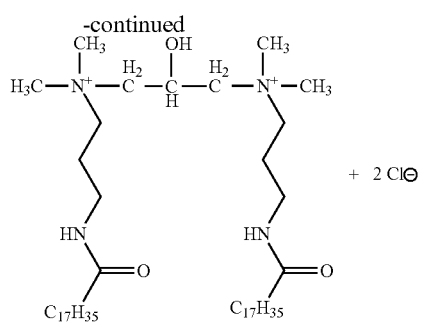

Reaction Scheme 3:

Like in Reaction Scheme 2, this scheme uses two moles of tertiary amine with one mole of an acid, and the linker is derived from epichlorohydrin. However, in this reaction scheme, the acid is para-toluenesulfonic acid (PTSA). The result of this aspect of Reaction Scheme 3 is that half of the negative counter ions for this GQ are the toluenesulfonate anion, while the other half required to achieve charge balance is chloride. Organic sulfonate counter ions, especially aromatic ones, are desirable in some cases because they impart useful properties to the compositions of the present technology, e.g., they promote vesicle formation.

SCHEME 3

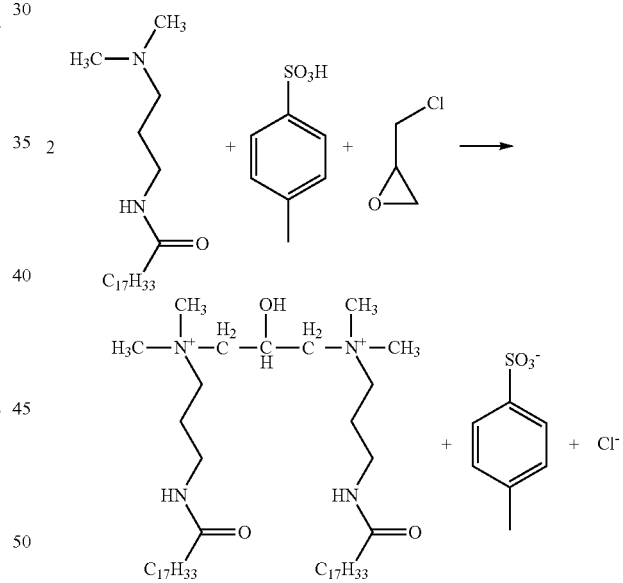

The notation for this GQ also differs from that in Reaction Scheme 2, because the hydrophobe is oleyl in this case instead of stearyl ($C_{17}H_{33}$ instead of $C_{17}H_{35}$). The presence of double bonds in fatty acids and their derivatives is commonly notated by the number of carbon atoms in the fatty acid followed by a colon followed by the number of double bonds in the molecule. Thus oleic acid may be notated by 18:1. Applying this notation to the GQ notation described earlier, the GQ from Scheme 3 becomes 18:1APDMA-3(OH)-18:1APDMA. The counter ions in the GQ are not specified in the shortened notation.

Reaction Scheme 4:

This reaction scheme uses a diglycidyl compound to form the linker.

SCHEME 4

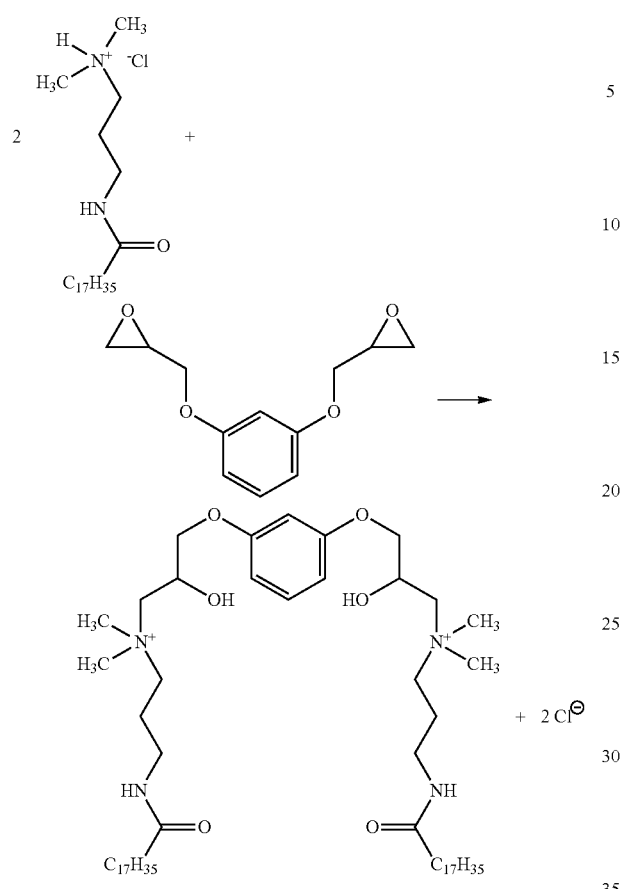

In this scheme, the diglycidyl compound is resorcinol diglycidyl ether (RDGE). For reactions of amines with diglycidyl linkers, the amines are first fully neutralized with an acid (typically hydrochloric, PTSA or xylene sulfonic acid). The amine salt then reacts with the oxirane functionalities of the diglycidyl compound to form the GQ. When using the shortened notation for GQs from diglycidyl compounds, an abbreviation for the diglycidyl compound is used, i.e., 18APDMA-RDGE-18APDMA for this GQ (no indication is used for the two hydroxyls in this case).

Note that this scheme may be used to produce compounds free from halide salts by the use of sulfonic acid to neutralize the amines. Other diglycidyl ethers (DGE), such as triethyleneglycol DGE, butanediol DGE and bisphenol DGE may also be used.

Reaction Scheme 5:

SCHEME 5

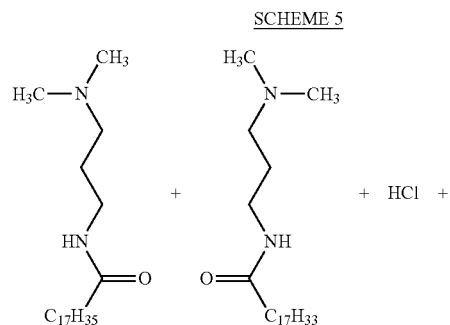

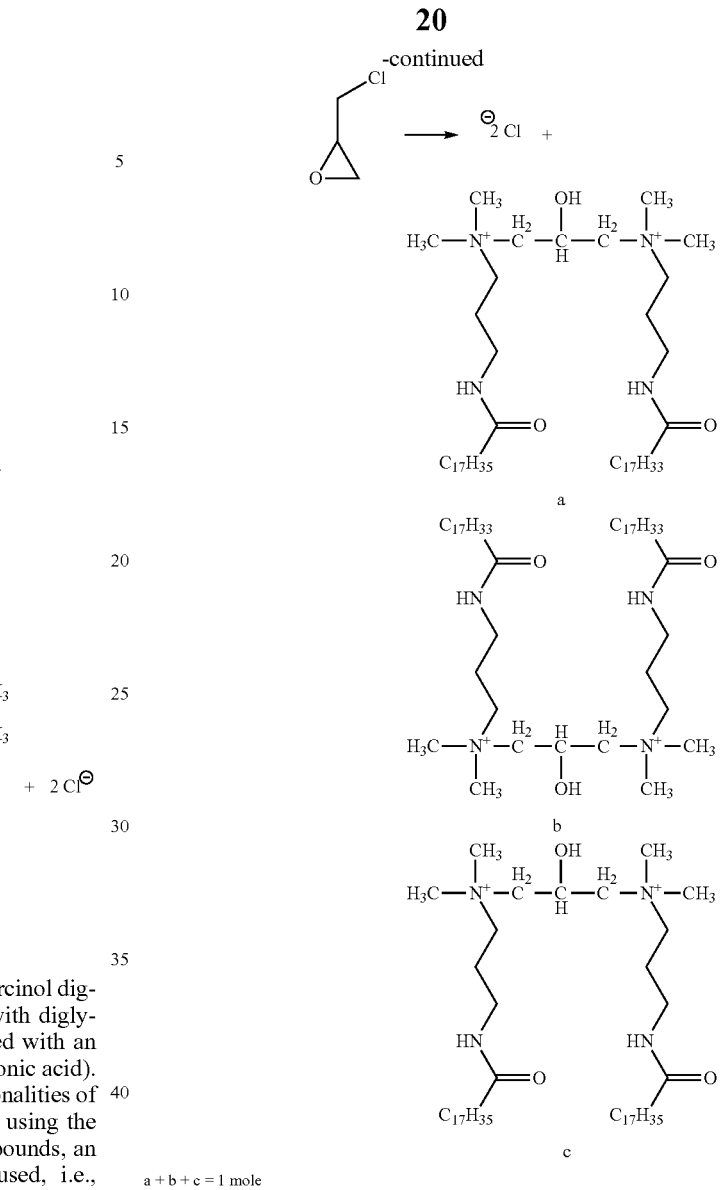

Reaction Scheme 5 uses a mixture of different amidoamines to make a random mixture of GQs. In this case, two different kinds of amidoamines (stearyl=18 and oleyl=18:1) are used in equimolar amounts. When a mixture of amines is used, the product composition is a statistical mixture determined by the relative reactivities and concentrations of the different amines. Any number of different amidoamines may be used, so long as the total moles of tertiary amine are sufficient to react with 1 mole of the substrate (epichlorohydrin in this scheme).

The product mixture of this example contains 18APDMA-3(OH)-18APDMA, 18:1APDMA-3(OH)-18APDMA, and 18:1APDMA-3(OH)-18:1APDMA.

Reaction Scheme 6:

In this scheme, an amidoamine (stearamidopropyldimethylamine) is used with a bis-hydroxyethyl-alkylamine to make a GQ composition with 1,3-dichloro-2-propanol as the substrate to provide the linker in the GQ. As discussed above, when a mixture of amines is used, the product composition is a statistical mixture determined by the relative reactivities and concentrations of the different amines, which is called a random GQ composition in the present technology. Any number of different amidoamines and alkylamines may be used, so long as the total moles of tertiary amine are sufficient to react with 1 mole of the linker.

The linker in this case (2-hydroxypropyl) is the same as that derived from using epichlorohydrin as a substrate. For shortened notation, the hydroxyethyl group is abbreviated by HE with a subscript 2 because there are two of them. This mixture consists of 18APDMA-3(OH)-18HE$_2$, 18HE$_2$-3(OH)-18HE$_2$, and 18APDMA-3(OH)-18APDMA.

Reaction Scheme 7:

This reaction scheme shows a method for preparing a random GQ composition from an amidoamine (stearamidopropyldimethylamine) and an ester amine, using epichlorohydrin as the substrate. Shortened notation for ester amines is EA, with a subscript to indicate the number of hydrophobe substituents on the nitrogen that have ester bonds. Thus, 18EA$_1$-3(OH)-18EA$_1$ is the third GQ shown in Reaction Scheme 7 in which both quaternary nitrogens have hydrophobe substituents with ester bonds.

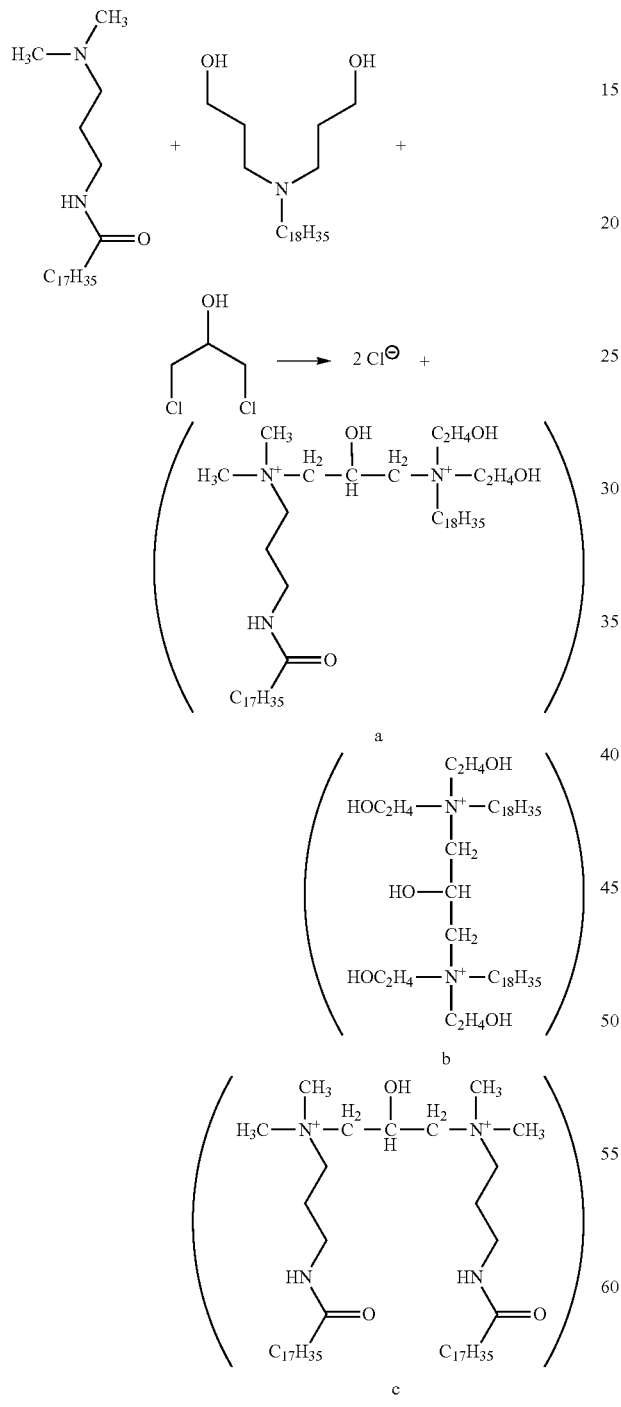

SCHEME 6

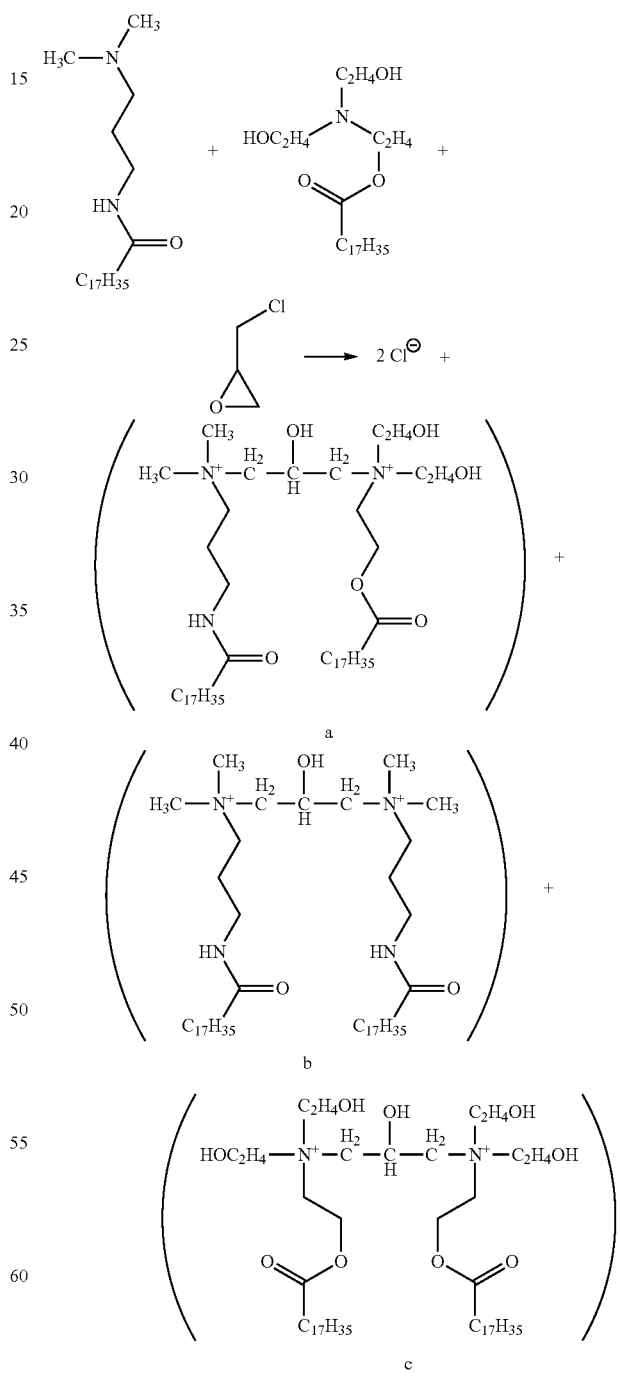

SCHEME 7

Reaction Scheme 8:

As shown in Reaction Scheme 8, a GQ composition is prepared from the substrate 1,2-dichloroethane and a carboxamidine, 1-hydroxyethyl-2-heptadecenyl-2-imidazoline.

SCHEME 8

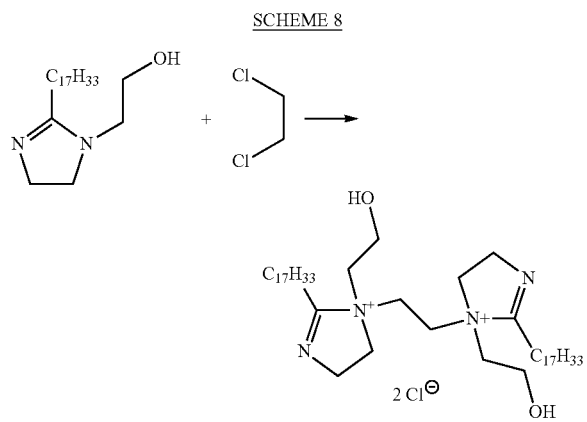

Reaction Scheme 9:

In this scheme, a non-fatty acid carboxylic acid derivative is used to prepare a GQ composition. As in Reaction Scheme 2, two moles of a fatty acid derived amidopropyldimethylamines are provided as the tertiary amines and the linker is derived from epichlorohydrin. However, this bis-quat is not prepared using HCl, but instead using a dicarboxylic acid derivative, ortho-phthalic anhydride. The nucleofuges from the epichlorohydrin in this case may be formally considered to be one equivalent of chloride and one equivalent of alkoxide anion (derived from the ring opening of the oxirane). The alkoxide anion is "trapped" by subsequent reaction with the ortho-phthalic anhydride to form the phthalate half-ester. The carboxylate anion also formed during this process provides one equivalent of negatively charged counter ion to the cationic nitrogens. The additional equivalent of counter ion comes from the chloride equivalent. Compounds such as these, in which at least a portion of the counter ion is also covalently bound to the cationic molecule, provide certain desired performance effects in their compositions, such as increased water solubility, or improved viscoelastic, gellant, thickening or drag reducing properties.

SCHEME 9

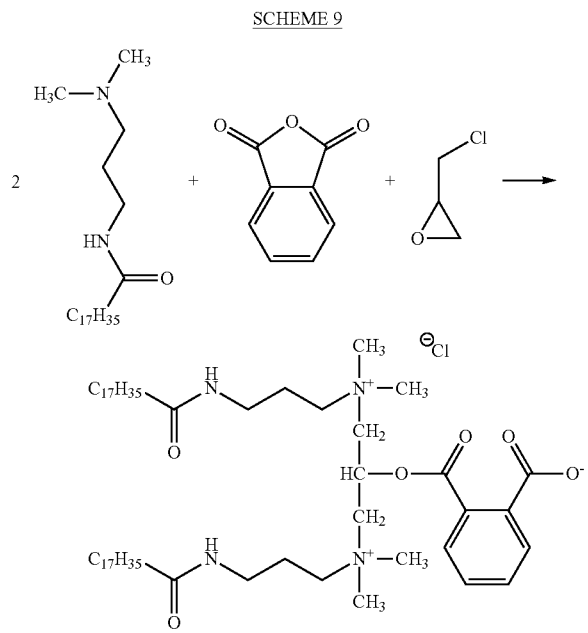

Dissymmetric or Structurally Defined Bis-Quats

In accordance with at least some embodiments, the presently described technology provides structurally defined bis-quats, which can be, for example, dissymmetric GQs or dissymmetric non-gemini bis-quats.

As used herein, a bis-quat composition is described as "structurally defined" if the distribution of the symmetric components in the polycationic composition is different from the distribution that would otherwise be obtained by the random process as described above. As used herein, "distribution of the symmetric components" means the pairings between $NR_1R_2R_3$ and $NR_4R_5R_6$.

Figure 3:
FIG. 3 is a schematic representation of at least one structurally defined bis-quaternary ammonium compound of the present technology, wherein the two cationic fragments are different.

Structurally defined bis-quats of the present technology can be formed through what can be called a stepwise process. Important points of the stepwise process include that at least two different kinds of amines of theoretical functionality 1 are used to provide two equivalents of amines that can react with one mole of a substrate of theoretical functionality 2, and also that the chemical reactions that form the bis-quats are conducted in such a way that dissymmetry or a substantial degree of structural definition in the product molecules is established. FIG. 3 schematically illustrates such a dissymmetric arrangement.

Each of the cationic fragments as shown in FIG. 3 can be derived from a mixture of different amines. Therefore two mixtures of different amines can be used for each of the cationic fragments. In accordance with at least one embodiment of the present technology, the compositions of the two mixtures must be different (different in chemical composition, in concentrations of like components, or both).

When mixtures of amines are derived from naturally occurring oils (vegetable or animal), then many of the fatty acid components are identical (although they may present in different amounts). If the two amine mixtures used for cationic fragments 1 and 2 of FIG. 3 differ only in the source of their fatty acid derived hydrophobes, then it is likely that a stepwise process for preparing polycationic quats will produce some polycationic components which are not dissymmetric. However, the distribution of the different fatty acids is relatively unique for each source. For example, fatty acids derived from soybean oil typically include about 7 different fatty acids. Corn oil fatty acids typically include about 5 different fatty acids, all of which are found in soya fatty acids, but in different proportions. Therefore, if cationic fragment 1 is soya derived, while cationic fragment 2 is corn derived, then the bis-quat composition from the two will contain symmetric components. However, the proportions of both symmetric and dissymmetric bis-quat components formed by the stepwise process are different from the proportions that are obtained when the stepwise process of the presently described technology is not used. When the amines are mixed before quaternization, in a process as described above for random GQ composition, a statistical mixture determined by the relative reactivities and concentrations of the different amines will result.

A person of ordinary skill in the art will also understand that while a reaction may be substantially selective for a certain leaving group over another, it is not necessary for it to be 100% selective for the purposes of the present technology. Thus, even when the amine mixtures used in the stepwise process have no common components, it is possible that some amounts of symmetric polycationic compounds are formed. Therefore, for purpose of the presently described technology, a bis-cationic composition is described as structurally defined if the distribution of the symmetric components in the polycationic composition is different from the distribution that would otherwise be obtained by a random process.

Preferably, the two amine mixtures are selected such that they have significant distinguishing features, such as alkoxylated amines with dimethyl substituted amines, or the fatty acid derived hydrophobes have distinguishing features such as degree of saturation and amounts of carbon chain lengths of about 18 and higher. The stepwise process can enhance the amounts of dissymmetric polycationic quats over what would be obtained by the random process as described above.

In accordance with the presently described technology, the structural definition of the polycationic compositions is typically apparent through its effect on physical properties of the viscoelastic compositions such as tendency to crystallize, melting point, solubility in water and other solvents, and in the rheological properties imparted to their solutions. Some or all of the properties of a structurally defined polycationic composition normally are different from a non-structurally defined polycationic composition made from the same components by a random process.

Similar to that for a bis-quat molecule in a random composition, the structure of dissymmetric bis-quat molecules in one or more structurally defined bis-quat compositions of the presently described technology can be represented by the following general formula:

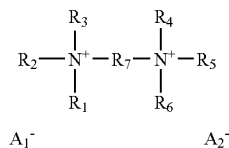

In some embodiments of dissymmetric bis-quat molecules of the present technology having this general structure, $R_2$, $R_3$, $R_4$, and $R_5$ can be members independently selected from (a) hydrocarbyl groups having from about 1 to about 4 carbon atoms, or (b) substituted hydrocarbyl groups having from about 1 to about 4 carbon atoms. Alternatively, $R_2$ and $R_3$ can be members of a heterocyclic ring, preferably a heterocyclic ring containing 5 or 6 carbon atoms. In such embodiments, $R_4$ and $R_5$ can be members of a different heterocyclic ring, or can be independently selected from group (a) as defined above or group (b) as defined above. When $R_4$ and $R_5$ are members of a different heterocyclic ring, that ring preferably contains 5 or 6 carbon atoms.

Additionally, in some embodiments of such dissymmetric bis-quat molecules of the present technology, $R_1$ and $R_6$ can be members independently selected from group (a) as defined above, group (b) as defined above, or (c) hydrocarbyl groups having from about 13 to about 40 carbon atoms or substituted hydrocarbyl groups having from about 13 to about 40 carbon atoms. In some such embodiments, the hydrocarbyl groups or substituted hydrocarbyl groups of group (c) can comprise carboxamides, carboximides, polycarboxamides, polycarboximides, carboxamidines, carboximidines, carboxylic esters, polycarboxylic esters, carboxylic acids, polycarboxylic acids, carboxylates, polycarboxylates, or combinations thereof.

In some particularly preferred embodiments, at least one of $R_1$ or $R_6$ is a member of group (c), and in some such embodiments, can further comprise a cyclo hydrocarbyl ring or a heterocyclic ring. In some embodiments, $R_1$ and $R_6$ are both chosen from group (c), while in others, only $R_1$ or $R_6$ is chosen from group (c). In at least one embodiment, $R_1$ is selected from group (c) and $R_6$ is selected from group (a) or group (b). In at least one embodiment, each of $R_4$, $R_5$, and $R_6$ is a hydrocarbyl group having from about 1 to about 4 carbon atoms or a substituted hydrocarbyl groups having from about 1 to about 4 carbon atoms. In some preferred embodiments, at least one of $R_1$ or $R_6$ is derived from a carboxylic acid having from about 13 to about 40 carbon atoms, and more preferably from about 16 to about 22 carbon atoms. In some particularly preferred embodiments, the carboxylic acid is derived from an animal or vegetable oil.

Moreover, in embodiments of dissymmetric bis-quat molecules of the present technology, at least one of $R_1$, $R_2$, or $R_3$ is different from each of $R_4$, $R_5$ and $R_6$.

It should be appreciated that the hydrocarbyl groups of groups (a), (b) and (c) can be arranged in any chemically rational combination, including aliphatic, aromatic, acyclic or cyclic.

In embodiments of the present technology where any of $R_1$ to $R_6$ are selected from group (b), the substituted hydrocarbyl groups of group (b) can have one or more substituents selected from hydroxyl (—OH), alkoxy, aryloxy, carbonate ester, carbamate, sulfonate, phosphinate, phosphite, phosphate, phosphonate, or combinations thereof. In some such embodiments, the alkoxy or aryloxy substituents have the general formula —OR, where R is a hydrocarbyl group having from about 1 to about 4 carbon atoms.

In the formula provided above for a general structure of a dissymmetric bis-quat molecules of the present technology, $R_7$ can be a member selected from the group consisting of hydrocarbyl groups having from about 2 to about 30 carbon atoms, and substituted hydrocarbyl groups having from about 2 to about 30 carbon atoms. For example, in some embodiments of the present technology, $R_7$ comprises hydrocarbyl groups having from about 3 to about 8 carbon atoms or substituted hydrocarbyl groups having from about 3 to about 8 carbon atoms. In preferred embodiments of this type, $R_7$ has a linear configuration. As another example, in some embodiments of the present technology, $R_7$ comprises hydrocarbyl groups having from about 9 to about 21 carbon atoms or substituted hydrocarbyl groups having from about 9 to about 21 carbon atoms. In preferred embodiments of this type, $R_7$ has a configuration comprising a ring structure. In yet another preferred embodiment, $R_7$ comprises a substituted aromatic ring or rings.

In embodiments of the present technology where any of $R_7$ is a substituted hydrocarbyl group, the hydrocarbyl group can have one or more substituents selected from hydroxyl, alkoxy, aryloxy, ester carbonate, carbamate, sulfonic acid, sulfonate, phosphinic acid, phosphinate, phosphorous acid, phosphite, phosphoric acid, phosphate, phosphonate or combinations thereof. In some such embodiments, the alkoxy or aryloxy substituents have the general formula —OR, where R is a hydrocarbyl group having from about 1 to about 4 carbon atoms.

There are several characteristic that can be preferred for $R_7$ as used in the present technology. For example, in at least some particularly preferred embodiments, $R_7$ is hydrophilic. As another example, in some embodiments, $R_7$ is a substituted aromatic group. As yet another example, in at least some embodiments, $R_7$ is a substituted hydrocarbyl group that is not a hydroxyalkylene.

In different embodiments of the present technology, $R_7$ can be derived from various sources. For example, in some preferred embodiments, $R_7$ is derived from a substrate including two reactive sites with different reactivities. As another example, $R_7$ can be derived from a di-sulfonic acid ester of a primary diol, a secondary diol, a derivative thereof, or a combination thereof. As another example, $R_7$ can be derived from an epihalohydrin. Further, $R_7$ can be derived from a bis-glycidyl ether. In at least some embodiments, $R_7$ can be derived from a di-haloalkyl hydrocarbon containing from about 2 to about 12 carbon atoms in which the two halogen atoms are attached to different primary or secondary saturated carbon atoms, and wherein the two halogen atoms have different reactivities. In some such embodiments, the two halogen atoms are different. In some embodiments, the di-haloalkyl hydrocarbon can be substituted with one or more additional hydroxy, alkoxy, or aryloxy substituents, and the additional substituents are not attached to one of the halogen-bearing carbon atoms. Further, the di-haloalkyl hydrocarbon can have a primary bromoalkyl group and a secondary chloroalkyl group.

The anion groups $A_1$ and $A_2$ in the above formula are selected independently and can be:

1) negatively charged inorganic ions;
2) organic molecules with negatively charged functional group(s), which can be, but are not limited to, carboxylate, sulfonate or phosphate; or
3) negatively charged functional group(s) which are part of $R_1$, $R_2$, $R_3$, $R_4$, $R_5$, $R_6$ or $R_7$, which can be, but are not limited to, carboxylate, sulfonate or phosphate.

When there is one or more hydrophobe carbon chains attached to each quaternary nitrogen atom in the above formula, the bis-quat is a gemini-quat (GQ). When there is only one hydrophobe chain per two quaternary nitrogen atoms, the bis-quat is a non-gemini bis-quat. It has been surprisingly found that non-gemini bis-quats of the present technology having one hydrophobe on one quaternary nitrogen atom and no hydrophobe on the other quaternary nitrogen atom exhibit some particularly useful and unexpected properties. For example, these bis-quats have the ability to form viscoelastic gels over a broad range of salt concentrations (e.g. from about 5% by weight to about 75% by weight salt). Salt solutions (brines) with salt concentrations above about 20% by weight have densities substantially higher than that of water, and are used in well bore service fluids for the advantages the higher density or salt concentrations confer.

Some compositions and formulation techniques for solids-free brine solutions for use in well bore service fluids are taught in Completion and Workover Fluids, by Kenneth L. Bridges, SPE Monograph Volume 19 (Society of Petroleum Engineers, Richardson, Tex., 2000), the content of which is incorporated herein by reference. Such brine solutions can be formulated to a range of densities, from about 9.7 to about 22.5 pounds per gallon, for use in aqueous completion fluids where their higher density relative to water is advantageous. For example, in the well completion process, a transition from a drilling or stimulation process is made as the well bore is prepared to produce hydrocarbons. The completion fluid serves to control formation pressures, and may also provide protection against or removal of formation damage.

Examples of brine solutions that can be suitable for use with the present technology can contain one type of salt, or can contain combinations or mixtures of salts. For example, some brine solutions contain water and up to about 25% or about 26% by weight sodium chloride, up to about 24% by weight potassium chloride, up to about 47% by weight sodium bromide, up to about 40% by weight calcium chloride, or up to about 66% by weight calcium bromide. Some other examples of brine solutions contain combinations or mixtures of two or more salts. Brine solutions containing zinc bromide, for example, preferably also contain at least one or two other salts, such as calcium bromide and/or calcium chloride. One example brine containing zinc bromide for use in a completion fluid is a composition containing about 52.8% by weight zinc bromide ($ZnBr_2$), about 22.8% calcium bromide ($CaBr_2$), and about 24.4% water, with the resultant solution having a density of about 19.2 lb. per gallon at about 60° C.

Thickening or gellation of brine solutions can impart additional advantages, such as reduced fluid leak off into the formation and less formation damage. Particularly preferred embodiments of non-gemini bis-quats of the present technology can thicken brine solutions and form viscoelastic gels at levels of from about 3% by weight to about 10% by weight bis-quat by weight of the composition.

In the present technology, structural definition can be established by a stepwise process, in which, in the first step, one equivalent of a tertiary amine (or a mixture of tertiary amines) is reacted selectively at one reactive site on the substrate. This creates an intermediate cationic quaternary ammonium compound in which the quaternary nitrogen atom bears a substituent which has a nucleofuge, so that a subsequent substitution reaction may then be effected with a second equivalent of a different tertiary amine (or a different mixture of tertiary amines). At the conclusion of the second step, the composition contains bis-quats, which are structurally defined in that, for at least a preponderance of the molecules, each molecule contains one cationic nitrogen derived from the first step (first equivalent of tertiary amine(s)) and one cationic nitrogen atom derived from the second step (second equivalent of tertiary amine(s)). To effect this stepwise process, it is necessary to achieve substantial selectivity between the reactions with the two leaving groups on the substrate.

The substrate to provide the linker fragment of the dissymmetric bis-quaternary ammonium compound of the present technology can be designated by the following structure:

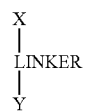

X and Y represent atoms or functional groups of atoms attached to the reactive carbon atoms on the substrate. The carbon atoms are reactive in that X and Y are suitable nucleofuges in substitution reactions with tertiary amines. Furthermore, the reactive sites on the substrate are reactive to different degrees under suitable conditions, so that a substitution reaction may happen at one site while leaving the other reactive site substantially intact.

For example, X and Y may be different pairs of halogen atoms, especially chlorine and bromine, or chlorine and iodine. Chloroalkyl groups are generally less reactive than either bromoalkyl or iodoalkyl groups in substitution reactions, when the alkyl groups are the same. By carefully controlling reaction conditions to minimize reaction at the reactive site bearing a chlorine atom, selective reaction at a reactive site bearing either a bromine or an iodine atom may be effected in the first step as described above. In the second step, additional amine can be reacted with the chloroalkyl group under conditions sufficient to effect that reaction, thus generating the structurally defined bis-quats.

Other factors can also enhance the reaction selectivity between the reactive sites on the substrate. For example, a primary carbon is generally more susceptible to substitution reactions than a secondary carbon atom because of steric hindrance. A primary bromoalkyl reactive site is generally more reactive than a secondary bromoalkyl group, which is generally more reactive than a secondary chloroalkyl group (which is less reactive than a primary chloroalkyl group). Thus, a primary bromoalkyl group can be reacted with greater selectivity in the presence of a secondary rather than primary chloroalkyl group. Additional factors that affect the reactivities of substrates in substitution reaction are described more thoroughly in Chapter 10 of the fifth edition of *March's Advanced Organic Chemistry*, by Michael B. Smith and Jerry March (2001), which is incorporated herein by reference. Within that chapter, leaving groups are ranked by their ability to become a nucleofuge in substitution reactions at saturated carbon atoms. Suitable pairs of X and Y may be selected from those rankings such that suitable reaction selectivity is attained. To achieve the dissymmetric bis-quats described here, it is sufficient that the X and Y groups are attached to reactive sites which may be reacted first at a preponderance of one site followed by a second reaction at the remainder of the sites.

Figure 4:
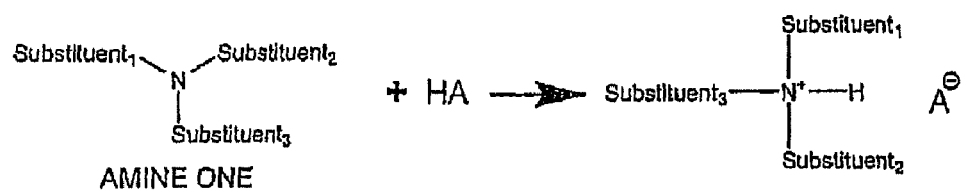
FIG. 4 is a schematic representation of at least one stepwise method of making a structurally defined bis-quaternary ammonium compound of the present technology, wherein the substrate to provide the linker is an epihalohydrin.
Figure 4:
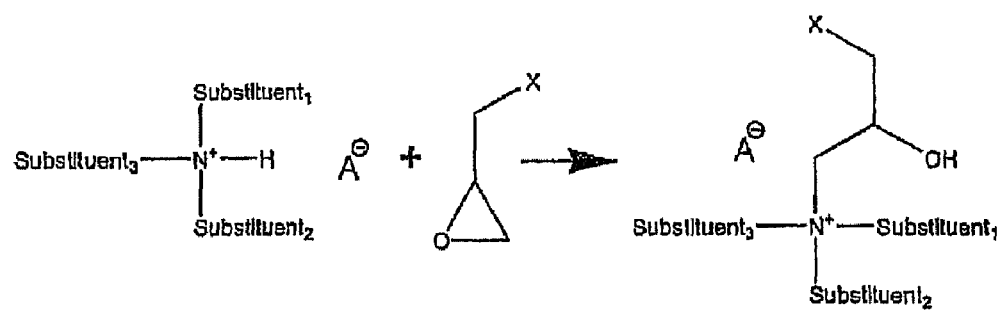
Figure 4:
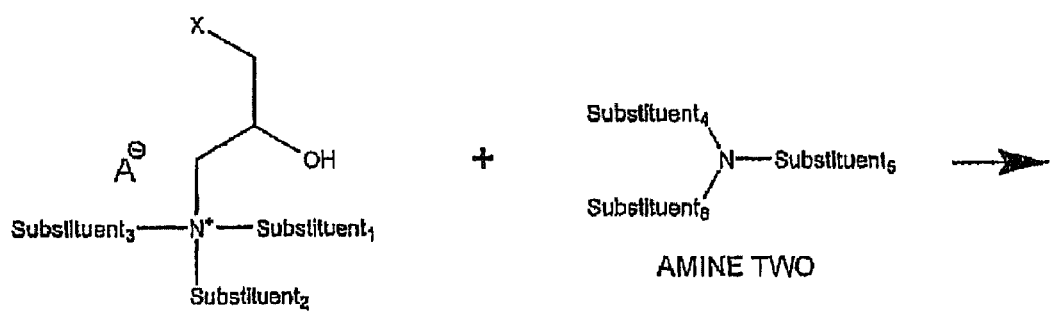
Figure 4:
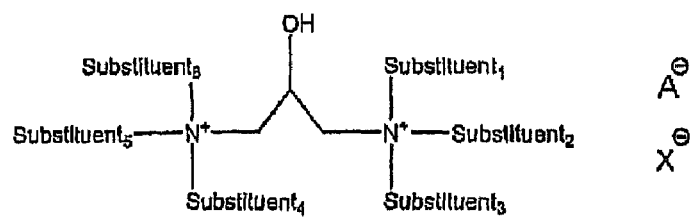

One category of preferred substrates in this process is epihalohydrins. In an epihalohydrin, X and Y are a chloromethyl group and an oxirane functional group. As illustrated in FIG. 4, substantially selective reaction with the oxirane functionality can be effected. In FIG. 4, first, a first equivalent of tertiary amine(s) is neutralized with an acid so that only tertiary hydrogen ammonium salts are present. These ammonium salts are then reacted with the epihalohydrins through the oxirane functionality. Because, essentially, no free amine is present, little or no reaction occurs at the halomethyl functional group. Once the reaction between the oxirane and ammonium salts is completed, the second equivalent of different tertiary amine(s) is reacted with the composition resulting from the first step. The free amine reacts with the halomethyl functional groups in this step, thus establishing the structural definition described earlier.

In FIG. 4, X can be a chlorine, bromine or iodine atom. HA is a neutralizing acid and A⁻ is the conjugate base of the acid. Non-exhaustive examples of suitable acids include hydrogen halides or their aqueous solutions; inorganic oxo acids, such as nitric acid; alkylsulfonic acids, such as methanesulfonic acid and alpha olefin sulfonic acids; alkylarylsulfonic acids such as toluenesulfonic acid, xylenesulfonic acid, and dodecylbenzenesulfonic acid; and arylakylsulfonic acids.

For example, in order to make a dissymmetric or structurally defined bis-quat using an epihalohydrin as the substrate, the first tertiary amine (or amine mixture), preferably a tertiary amidoamine, is first dissolved in a water compatible solvent. Water is used as a co-solvent at levels from about 1% to about 99% by weight of the solvent composition. Acid can then be added slowly to the solution in sufficient quantity to react with all of the first tertiary amine. Once neutralization of the amine is completed, epihalohydrin can be added to the solution slowly, typically from about 15 minutes to about 2 hours. The temperature during the addition of the epihalohydrin is preferably from about 25 to about 100° C. The total charge of epihalohydrin is preferably from about 1.0 to about 1.2 moles per mole of the first tertiary amine. Preferably, a slight excess of epihalohydrin, such as about 1.03 moles per mole of first tertiary amine, is used to effect more complete quaternization so that low levels of free amine and amine salt are present in the final product.

After the epihalohydrin charge is complete, the process can be continued until reaction of the first amine is complete. Reaction degree of completion for the first amine may be determined by titration methods, for example by titration for residual free amine and amine salt levels. If necessary, additional epihalohydrin is charged to reduce levels of free amine and amine salt to acceptable levels. Acceptable levels for the first step are preferably such that at least about 90% of the total amine equivalents charged are converted to quaternary ammonium compounds (about 90% molar conversion). Once reaction of the first amine is sufficient, a second amine (preferably different from the first amine) is slowly charged to the solution from step 1, preferably over from about 15 minutes to about 4 hours. The amount of second amine charged is about one mole per mole of epihalohydrin. The temperature during the addition of the second amine is preferably from about 25° C. to about 100° C. Again, the process is continued until degree of reaction, as determined by titration methods, is acceptable. If necessary, additional epihalohydrin may be charged to achieve an acceptable level of reactant conversion, such as about 90% molar conversion minimum to quaternary ammonium compounds. Once the degree of conversion is acceptable, properties such as actives concentration and pH can be adjusted (if desired) through the addition of additional solvents (for actives) and acids or bases (for pH adjustment).

The following reaction schemes provide more specific illustrations of the stepwise process and the structurally defined compositions of the presently described technology.

Reaction Scheme 10:

Reaction Scheme 10 uses the same components in the same ratios as those in Reaction Scheme 5 described above. Unlike Reaction Scheme 5, which produces a statistical mixture (i.e., a random GQ composition) determined by the relative reactivities and concentrations of the different amines, Reaction Scheme 10 produces structurally defined GQ composition containing a much higher amount of the dissymmetric 18APDMA-3(OH)-18:1APDMA, and much less of 18:1APDMA-3(OH)-18:1APDMA and 18APDMA-3(OH)-18APDMA.

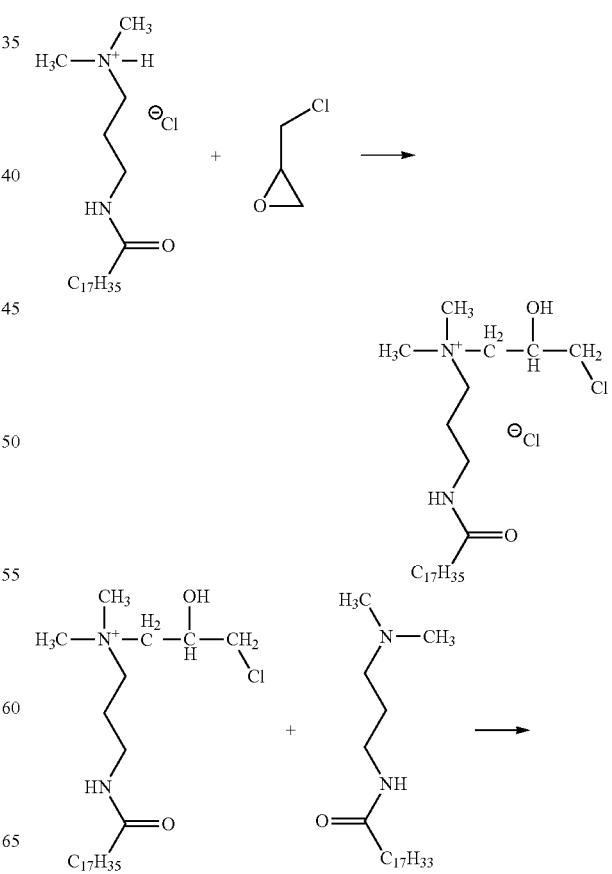

SCHEME 10

-continued

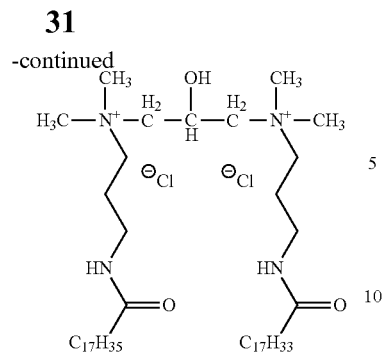

Such a structurally defined composition is often preferred, because while the 18APDMA component can provide superior viscoelasticity and higher viscosity over the 18:1AP-DMA, 18APDMA-3(OH)-18APDMA is a solid at about 42 wt % active ingredients in a mixture of water and 2-propanol, and it is more difficult to handle for making viscoelastic solutions or gels. Furthermore, 18APDMA-3(OH)-18AP-DMA based viscoelastic solutions tend to become hazy to opaque around room temperature, because of the tendency of the saturated C18 hydrophobe to cause the bis-quat to crystallize. On the other hand, 18:1APDMA-3(OH)-18:1AP-DMA is a soft paste at about 50 wt % active ingredients in water and 2-propanol, so it is easier to handle for making viscoelastic solutions or gels. 18:1APDMA-3(OH)-18:1AP-DMA can provide clear viscoelastic gels at room temperature, but it does not provide viscosities as high as the 18APDMA-3(OH)-18APDMA, especially at higher temperatures. The dissymmetric 18APDMA-3(OH)-18:1AP-DMA bis-quat, on the other hand, is a liquid at room temperature in an about 50 wt % active ingredient solution with 2-propanol and water. Furthermore, its viscoelastic solutions or gels are clear to slightly hazy at room temperature and have higher viscosity than comparable gels made from 18:1AP-DMA-3(OH)-18:1APDMA.

A person of ordinary skill in the art will understand that commercially available stearic (C18) and oleyl (C18:1) derivatives typically contain from about 5% to about 40% (by weight) of other fatty acid components (which were not represented in the scheme below). If the other components are taken into consideration, the compositions are still structurally defined, with enhanced amounts of the dissymmetric 18APDMA-3(OH)-18:1APDMA bis-quat.

Reaction Scheme 11:

This reaction scheme uses the same components as those in Reaction Scheme 6 described above. Scheme 11 does not give the statistical mixture of random bis-quats produced in Scheme 6, but gives an enhanced level of dissymmetric bis-cationic 18APDMA-3(OH)-18HE$_2$, and less of the symmetric bis-cationic 18HE$_2$-3(OH)-18HE$_2$ and 18APDMA-3(OH)-18APDMA. This scheme also illustrates the use of para-toluenesulfonic acid for producing structurally defined bis-cationic compounds.

SCHEME 11

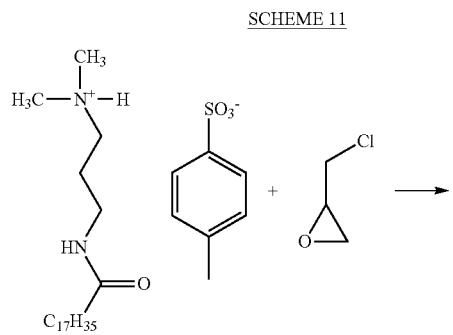

-continued

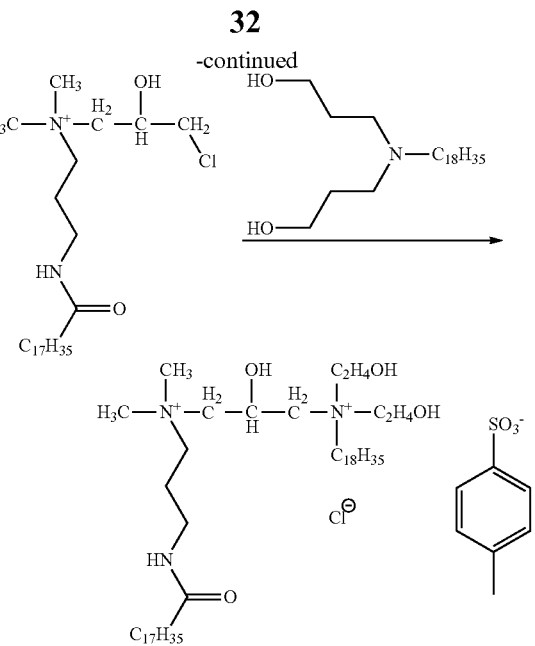

Similarly, Reaction Scheme 7 described above can also be modified to a two step process, which would produce a structurally defined composition with enhanced 18EA$_1$-3(OH)-18APDMA.

Reaction Scheme 12:

Reaction Scheme 12 illustrates the process for preparing a structurally defined bis-quat composition from alkylamine derivatives. The tallow amine derivative (ethoxylate) is a mixture in which the alkyl chains are those which occur in animal tallow. For example, bovine fat tallow derived amine may contain $C_{14}$-$C_{18}$ chains, which typically contain combinations of from 0 to 3 double bonds. The other amine, erucyldihydroxyethylamine, is typically derived from high erucic (C22:1) rapeseed oil. Only the enhanced dissymmetric component, (14-18)HE$_2$-3(OH)-(22:1)HE$_2$, is represented in the scheme below.

SCHEME 12

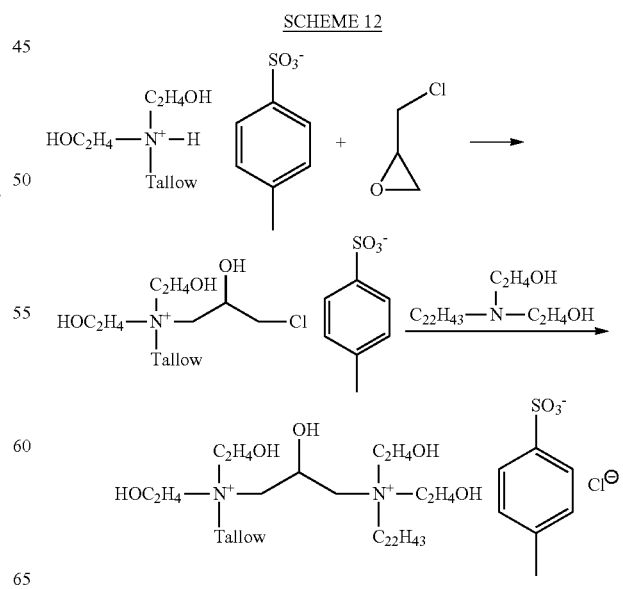

Reaction Scheme 13:

Reaction Scheme 13 as shown below illustrates a particularly useful process and composition for structurally defined polycationic compositions.

The first equivalent of amines is a mixture of amidoamines derived from high erucic rapeseed oil (HEAR), which has an especially high concentration of C22:1 hydrophobe chain length, but also includes $C_{16}$-$C_{20}$ chains with from 0 to 3 double bonds. The second step uses an amine mixture derived from soybean oil (Soya), which includes C12-18:i, where i may be from 0 to 3. The resulting structurally defined composition is particularly desirable because it combines a component from HEAR amidoamine that can give excellent rheological properties to aqueous compositions when being incorporated into a bis-quat, but has a higher cost, with a component from Soya amidoamine that has a low cost and can gives moderate performance when being incorporated into a bis-quat. In such a way, the properties of the structurally defined bis-quat are superior to a blend of the two separate bis-quats based on either HEAR amidoamine or Soya amidoamine only.

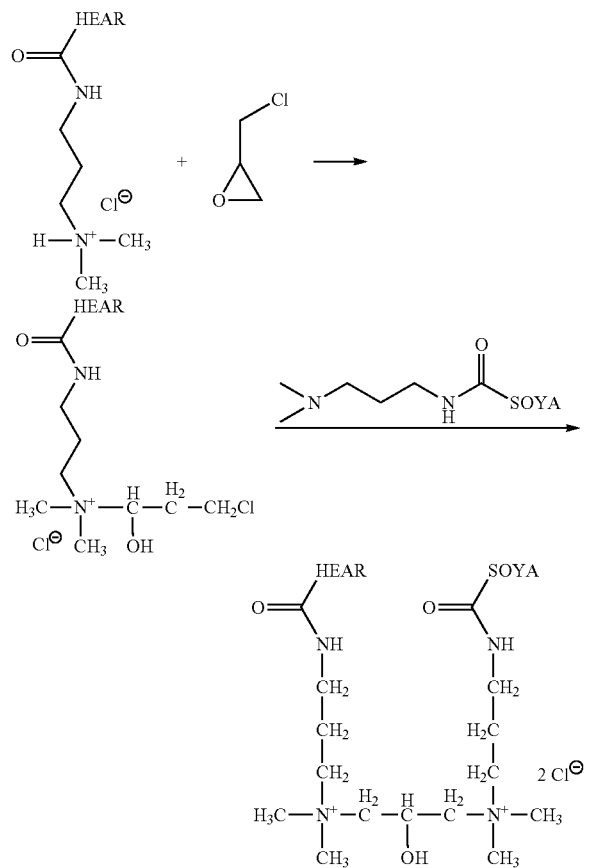

SCHEME 13

Modified Polycationic Compounds

In accordance with an other embodiment, the present technology provides modified polycationic compositions in which the polycationic molecules have additional chemical functional groups that, for example, may be anionic at some pH ranges. These modified polycationic compositions can be obtained by chemical reactions subsequently performed on polycationic molecules already formed or concurrently with the formation of the polycationic molecules. Modified polycationic compositions having a substantial degree of structural definition are especially desired in the present technology.

For example, one group of the modified polycationic compounds providing useful properties are polycationic carboxylates ("PCCs"). A PCC can be formed by acylation of a polycationic compound with a dicarboxylic acid anhydride. The polycationic compound must have a hydroxyl functional group (or groups), such as the hydroxyl group formed through quaternization tertiary amines with an epihalohydrin. The new product has the original polycationic components plus a new ester linkage and either a carboxylic acid or carboxylate anion functional group. Since an acid anhydride reacts with water and other hydroxylic materials, those must be substantially removed before starting acylation of the polycationic compound. The free acid group generated by the acylation is preferably neutralized, but not necessarily.

PCCs of the present technology demonstrate unexpected and useful results, and they can greatly reduce or completely eliminate the requirement for salts, cationic surfactants, or other additives. Use of PCCs in viscoelastic compositions of the present technology can be particularly desirable in applications when salts are not available, or when possible ground contamination with salts is not acceptable.

In at least one embodiment using a PCC of the present technology, a viscoelastic composition is provided that comprises water and an effective amount of at least one polycationic quaternary ammonium compound to control the viscoelasticity of the composition, wherein the at least one polycationic quaternary ammonium compound comprises a carboxylate functional polycationic quaternary ammonium compound. In at least one preferred embodiment, the carboxylate functional polycationic quaternary ammonium compound is produced by converting at least one alkoxide nucleofuge in a quaternary ammonium compound to a carboxylate group with an acid anhydride.

In at least one embodiment, a polycationic carboxylate of the present technology has the following general formula:

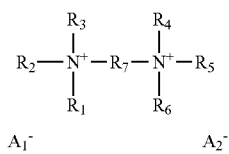

In the general structure set forth above, $R_7$ is preferably a carboxylate anion containing from about 2 to about 24 carbon atoms. $R_1$ through $R_6$ can be selected according to the descriptions set forth above for other types of gemini bis-quaternary compounds of the present technology. For example, in at least some embodiments, $R_2$, $R_3$, $R_4$, and $R_5$ can be independently selected from: (a) hydrocarbyl groups having from about 1 to about 4 carbon atoms; or (b) substituted hydrocarbyl groups having from about 1 to about 4 carbon atoms. Alternatively, $R_2$ and $R_3$ can be members of a heterocyclic ring, and $R_4$ and $R_5$ can be members of a different heterocyclic ring or can be independently selected from group (a) as defined above or group (b) as defined above.

In some embodiments, $R_1$ and $R_6$ can be members independently selected from: group (a) as defined above; group (b) as defined above, or (c) hydrocarbyl groups or substituted hydrocarbyl groups, wherein the hydrocarbyl groups or substituted hydrocarbyl groups have from about 13 to about 40 carbon atoms and comprise carboxamides, carboximides, polycarboxamides, polycarboximides, carboxamidines, carboximidines, carboxylic esters, polycarboxylic esters, carboxylic acids, polycarboxylic acids, carboxylates, polycarboxylates, or combinations thereof. In some preferred embodiments, at least one of $R_1$ or $R_6$ is a member of group (c), and can further comprise a cyclo hydrocarbyl ring or a heterocyclic ring In polycationic carboxylates of the present technology, anions $A_1^-$ and $A_2^-$ can be independently selected from: (i) negatively charged inorganic ions; (ii) organic molecules with one or more negatively charged functional groups; or (iii) negatively charged functional groups which are part of $R_2$, $R_3$, $R_4$, $R_5$ or $R_7$. In some particularly preferred embodiments, $A_1^-$ or $A_2^-$ is a negatively charged functional group which is part of $R_7$.

Preparation of a PCC of the present technology can begin with a precursor, such as either a random or structurally defined poly-cationic quat prepared by the methods described above. If an alcohol solvent has been used in preparing the precursor, the alcohol solvent must be removed by distillation, thin film evaporation, or any other suitable methods for removal of volatile solvents. Preferably, the precursor is prepared in a non-alcoholic solvent, such as acetone or methyl ethyl ketone ("MEK"). Water contained in the precursor solution must also be removed. Water removal ("drying") can be affected by azeotropic distillation of solvent from the precursor solution. Preferably, distillation is continued until the water content is about 0.5% or less of the active ingredient concentration (% wt.). Dry solvent can be added to replace the solvent and water removed during the drying process on an equal weight basis in order to maintain the active ingredient concentration. Water content can be determined by Karl-Fisher titration.

Once the precursor solution is dry, one mole of dicarboxylic acid anhydride can be charged to the solution. If the PCC is to be provided as a tertiary amine salt, then the tertiary amine may be charged at this point, also. If the PCC is to be provided as a metal salt, or an amine that would react with the anhydride functionality is used, the neutralization of the carboxylate can be obtained after the acylation step is completed in the pH adjustment step. The mixture can be heated to from about 30° C. to about 100° C. to facilitate dissolution and reaction of the acid anhydride. Completion of the acylation reaction can be determined by titration. As will be understood by those skilled in the art, the specific titration required depends on the form of the carboxylate, which can be in either acid or salt form. Once acylation is completed (preferably about 90% molar conversion to ester), properties such as actives concentration and pH can be adjusted (if desired) through the addition of solvents (for actives) and acids or bases (for pH adjustment).

Reaction Scheme 9 above shows an exemplary PCC which is obtained concurrently with the formation of the polycationic molecule. An alternate method of preparing this PCC is to prepare the GQ as in Reaction Scheme 2, and then acylate the hydroxyl group with ortho-phthalic anhydride in a separate step. An anhydride is employed in either method, and any solvents used must be dry and not react with the anhydride.

Exemplary Applications of Polycationic Quat Compositions

Polycationic compounds of the present technology are suitable for a wide variety of applications where thickened or gelled aqueous compositions are desired, including in agriculture, cleaners, personal care, disinfectants, gene transfer, etc.

For example, sprayed pesticides sometimes utilize additives to minimize spray drift. Some polycationic compositions of the present technology can be used as drift control agents to reduce spray drift.

For another example, gels formed from polycationic compositions of the present technology can be used to suspend granular pesticides, and other water insoluble agents. It is known that certain pesticides can be used in acid or acid salt form, such as the herbicide 2,4-dichlorophenoxyacetic acid. An acid pesticide can be incorporated into a process for preparing polycationic compositions of the present technology, such that the pesticide acid provides at least a portion of the counter ions to the cationic sites. Such compositions are multipurpose, in that the viscous gel will stick to leaves of the target plants to deliver more efficiently the herbicidal component. Such compositions can also be formulated with less volatile organic compounds and other inert ingredients (that are released into the environment) than are in current commercial products.

Some polycationic compositions of the present technology can be used in cleaners and cleansing gels to improve contact on vertical surfaces. For example, polycationic quats of the present technology can substitute polysaccharides in cleansing gels as those described in U.S. Pat. App. No. 2004/0097385, to Chen, et al., published on May 20, 2004, or can be used to make phase stable viscoelastic cleaning compositions as those described in U.S. Pat. No. 5,833,764, to Rader, et al., issued on Nov. 10, 1998, for opening drains.

Some polycationic compositions of the present technology can be used in personal care compositions, such as gel soaps, shampoos and conditioners. Some embodiments of polycationic compositions of the present technology can form stable aqueous viscoelastic solutions in water. In some embodiments, such viscoelastic solutions are clear, instead of hazy, opaque, or pearlescent, which can result in enhanced aesthetic properties in personal care compositions. Some embodiments of polycationic compositions of the present technology can provide or enhance conditioning properties in personal care compositions for skin and/or hair, such as rinsability, combability (on wet and/or dry hair), feel (on skin and/or hair), detangling, and static control. With respect to specific personal care compositions, some embodiments of polycationic compositions of the present technology can be used to substitute for some or all of the surfactants in aqueous viscoelastic surfactant solutions for the cleaning of hair or skin as those described in U.S. Pat. No. 5,965,502, to Balzer, issued on Oct. 12, 1999.

In at least one embodiment, a personal care composition using polycationic quats of the present technology can comprise a clear viscoelastic composition comprising water and least one polycationic quaternary ammonium compound comprising a bis-quaternary compound of the following general formula:

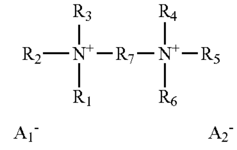

In the above formulation, $R_2$, $R_3$, $R_4$, and $R_5$ can be members independently selected from the group consisting of: (a) hydrocarbyl groups having from about 1 to about 4 carbon atoms; and (b) substituted hydrocarbyl groups having from about 1 to about 4 carbon atoms. Alternatively, $R_2$ and $R_3$ can be members of a heterocyclic ring, and $R_4$ and $R_5$ can be members of a different heterocyclic ring or are independently selected from group (a) as defined above or group (b) as defined above. In the polycationic quat structure, $R_7$ can be a member selected from the group consisting of hydrocarbyl groups having from about 2 to about 30 carbon atoms, and substituted hydrocarbyl groups having from about 2 to about 30 carbon atoms. Additionally, $R_1$ and $R_6$ can be members independently selected from the group consisting of group (a) as defined above; group (b) as defined above, and (c) hydrocarbyl groups having from about 13 to about 40 carbon atoms or substituted hydrocarbyl groups having from about 13 to about 40 carbon atoms. At least one of $R_1$ or $R_6$ should be a member of group (c) as defined above. Further, the anions, $A_1^-$ and $A_2^-$ can be independently selected from the group consisting of (i) negatively charged inorganic ions; (ii) organic molecules with one or more negatively charged functional groups; and (iii) negatively charged functional groups which are part of $R_1$, $R_2$, $R_3$, $R_4$, $R_5$, $R_6$, or $R_7$.

The ability of viscoelastic solutions using polycationic quats of the present technology to form stable suspensions having particulate material suspended therein is also beneficial in the personal care area. Examples of particulates include, for example, but are not limited to, anti-dandruff agents, abrasives (e.g., crushed walnut or apricot shells, silica, cellulose), sun block agents (e.g., zinc oxide), pigments and dyes, glitters, and micro-encapsulated materials (e.g., vitamins, minerals, fragrances, polymer beads), can be used in forming viscoelastic suspensions in personal care compositions.

Bleaching agents such as hydrogen peroxide can be gelled using polycationic compounds of the present technology to make thickened aqueous bleach compositions. For example, U.S. Pat. No. 4,800,036, issued Jan. 24, 1989 and European Patent No. EP 0298172, issued on Jan. 11, 1989, both to Rose, et al., teach aqueous bleach compositions thickened with a viscoelastic surfactant. Some polycationic quats of the present technology can be used for such applications. Some quaternary compounds of the present technology also have bactericidal properties.

Figure 14:
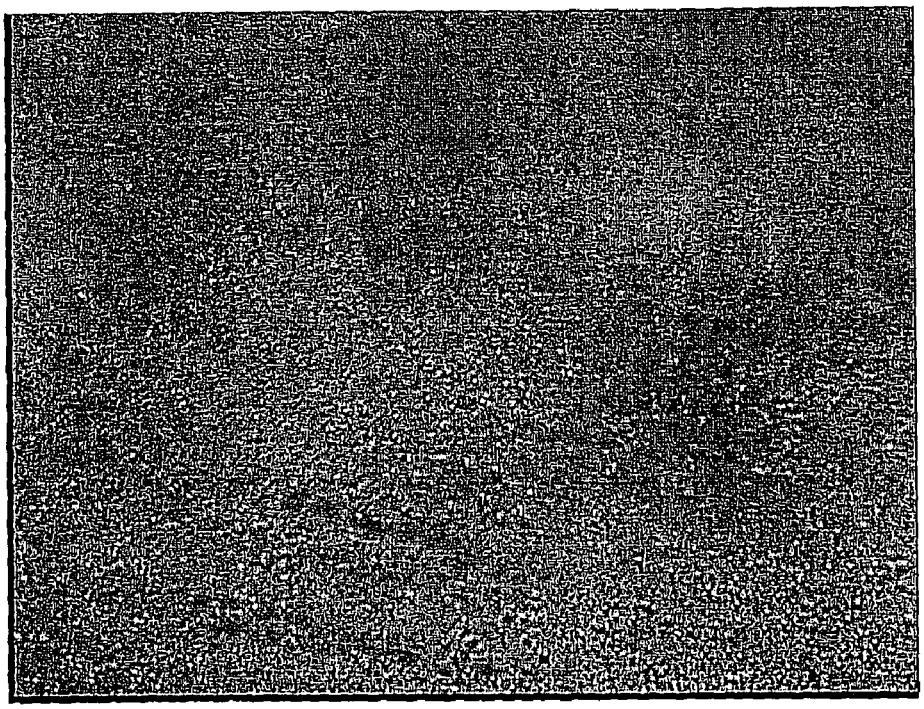
FIG. 14 shows vesicles of relatively uniform size distribution formed by hydration of a film of C65-GQ using 0.1 wt % $CaCl_2$. The magnification is 200×.
Figure 15:
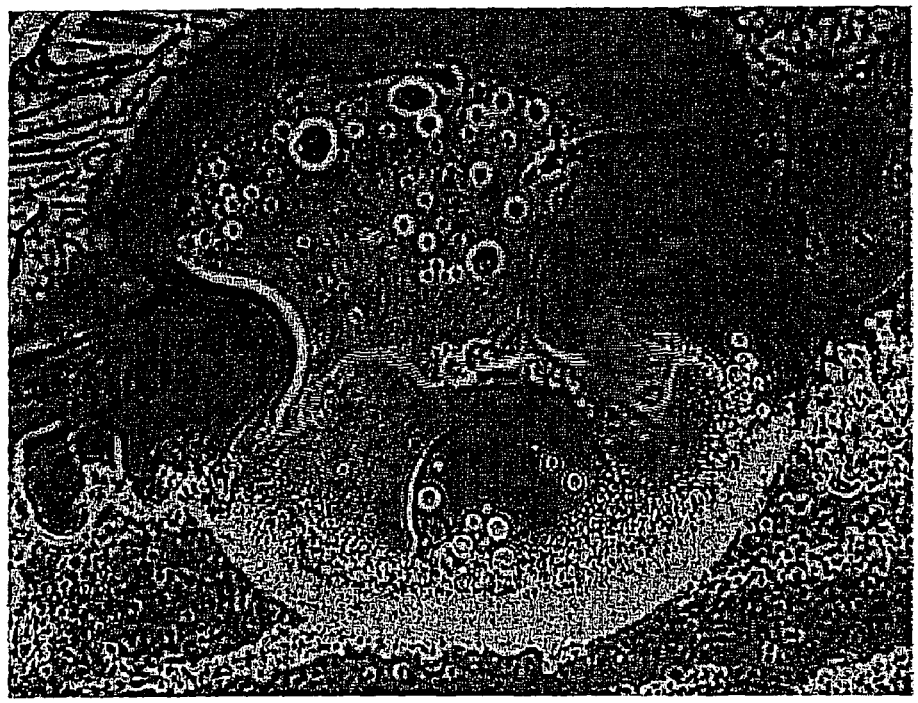
FIG. 15 shows vesicles being generated from a dried film of C65-GQ by hydration with 0.1% sodium xylene sulfonate.

The thickening and viscoelastic properties of viscoelastic compositions of the present technology may be related to vesicle formation, or other phenomena. As shown in FIGS. 14 and 15, some polycationic quats of the present technology have demonstrated vesicle formation.

As known in the art, micelles demonstrate a variety of forms, such as rod or worm-like. A key characteristic of micelles is that the surfactant molecules that make up the micelles are oriented such that the hydrophilic portions of the molecules form the outer surface around an internal core region, in which the hydrophobe portions of the molecules reside. The radius of the core is approximately equal to the length of the fully extended hydrophobe chain. The average number of surfactant molecules in a micelle is the aggregation number, and can range from several molecules to over a hundred for typical cationic surfactants. Micelles are dynamic structures in equilibrium with free surfactant molecules in solution. Surfactant molecules exchange into and out of micelles with high frequency. Because micelles are too small to be seen by light microscopy, electron microscopy is used.

Vesicle formation can provide additional useful properties other than thickening. Vesicles are more or less spherical surfactant self-assemblies. Essentially, a vesicle is a bilayer lamellar structure in which the edges have wrapped around and joined each other to form a sphere. Vesicles may have multiple bilayers, which creates concentric spheres. The core of a vesicle is a compartment that contains the aqueous solvent used to dissolve the surfactant initially, but essentially free of surfactants molecules. Vesicles may be manipulated in such a way that the internal compartment is used as a carrier for other molecules. The number of surfactant molecules that make up vesicles is much larger than are in micelles, usually about 10 to about 1000 times larger. Furthermore, although vesicles are also dynamic structures, the rate of exchanges of surfactant molecules in vesicles are much slower than those in micelles. As Zana describes vesicles at page 26 of Dynamics of Surfactant Self-Assemblies (2005), "the lifetime of a vesicle must be extremely long and vesicles can probably be considered as "frozen" on the laboratory times scale (weeks to months or years)" Many vesicles are large enough to be seen under a light microscope.

Another key feature of vesicles is that a vesicle has an inside and an outside. The inside encloses some of the aqueous phase, and possibly other molecules dissolved in the water. Vesicles can be used to deliver entrapped molecules into environments they might not normally have access to because of chemical instabilities, etc. In contrast, the interior of a micelle is in a "quasi-liquid state" according to page 14 of Dynamics of Surfactant Self-Assemblies, by Zana.

Spontaneous vesicle formation has been observed for GQs and PCCs of the presently described technology under a light microscope (illustrated in FIGS. 14 and 15). Vesicle formation has been observed when polycationic compounds are exposed to either dilute salt solutions or dilute solutions of anionic surfactant. PCCs have been observed to form vesicles in deionized water.

In the area of gene transfer, vesicles are synthetic analogs of liposomes—essentially naturally occurring biological vesicles. Synthetic vesicles can be infused with, for example, drug molecules. The vesicles can then be used to deliver the drug as part of treatment. Cationic vesicles have been found to be useful in gene therapy for the delivery of genetic material. However, conventional alkylamine and etheramine cationic compounds exhibit toxicity to many organisms that limits their in vivo use, while esteramine derived cationic compounds are less toxic, but also less stable. The amidoamine polycationic quats of the present technology have demonstrated vesicle formation and can be less toxic than alkylamine quats but more stable than esteramine derived quats.

Besides fracturing fluids as described earlier in this application, some polycationic compounds of the present technology can be used in other hydrocarbon recovery fluids in oil field, which include, for example, other stimulation fluids (such as acidizing fluids), drilling fluids, thickeners, completion fluids, diversion fluids, etc.

In oil field applications, acidizing is a process of pumping acid into a well bore to remove formation damage or other materials so that production is enhanced. In this process, thickened acids are desirable because they provide more efficient acidizing in certain types of subterranean zones, e.g., high permeability formations. Other acidizing applications use invert emulsions of aqueous acid in an oil, e.g., diesel or kerosene. Some polycationic compounds of the presently described technology as described above can be used as acid thickeners or to form invert emulsions with acid and oil.

Certain polycationic quat compositions of the present technology can also be used in drilling fluids. The special class of drilling fluids used to drill most deep wells is called drilling muds because of their thick consistency. Drilling muds normally require additional properties beyond simple drilling fluids that can prevent damage to the subterranean formation, prevent drill pipe corrosion and fatigue, and allow the acquisition of information about the formation being drilled. Drilling fluids and muds may be subclassified according to a number of characteristics, such as fluid phase alkalinity, water or oil continuous phase, etc. Besides polycationic quats of the present technology, drilling mud compositions can further include the traditional ingredients such as bactericides, corrosion inhibitors, emulsifiers, fluid loss and viscosity control agents, shale control additives, etc.

Water based drilling fluids use various polymers as thickeners to increase the viscosity of the drilling fluids and improve the fluids ability to remove cuttings. Some polycationic quats of the presently described technology can be used as thickeners for such drilling fluids or muds.

Thickeners suitable for use in oil based drilling fluids include organoclays. These are clays treated with various compounds to make them compatible with organic fluids. When placed in an oil based drilling fluid, they thicken the fluid, improving the fluids ability to carry the cutting to the surface. Some polycationic compositions of the present technology can be used as treatment compositions for making organoclays.

Some drilling fluids are water in oil emulsions. These emulsions often include brines which can adjust the density of the drilling fluid. Controlling the density of the drilling fluid is important to prevent formation damage and lose of drilling fluid. High density drilling fluids provide support to the surrounding formation that, under its own pressure, might collapse into the bore hole if lower density fluids were used. Formation preparation and hydrocarbon recovery would then be more complicated. The high electrolyte strength of high density brines can also reduce the permeation of well bore fluids into the formation (which must later be recovered), and they may reduce the hydration of shale and clay in the formation. Some polycationic quats of the present technology can be used for thickening or emulsifying the brines in the drilling fluids.

During the drilling operations, the subterranean formation and well bore casing come into contact with a variety of materials which can have adverse effects on further operations or hydrocarbon production. The casing pipe needs to be cemented and the cement needs to adhere to the formation and various materials used in the drilling fluid can prevent this. Completion fluids are used to wash these materials from the formation. Since the density of the completion fluids can affect the well bore similarly to the drilling fluids above, a variety of brines or other materials are used. Hydrocarbons, olefins, etc. are circulated to remove the oil based muds. Gelled pills are added to push these materials through the well. The gel forming properties of certain polycationic compounds of the present technology can provide compositions for these applications. Furthermore, gel pills are pushed through the well with other fluids such as brines, which may require viscosity modification. Some polycationic compounds of the present technology have shown to provide such viscosity modification to a variety of brines and water.

Another function of the completion fluid is to remove particulate matter and remnants of other materials used in the drilling operation from the casing, such as pipe dope. The various materials added to pipe dope can plug the formation and cause damage to the production zones. As these materials are removed from the joints in the casing string, they can settle out in the production zone. By viscosifying the completion fluid, this kind of settling can be minimized. Furthermore, the filter cake formed during the drilling operation often requires special treatments, such as enzymes or hydrogen peroxide, to effect sufficient removal. Some polycationic compound compositions of the present technology can provide useful, new or improved compositions for formulation of filter cake removal treatments.

Some completion fluids such as those that use zinc bromide, cesium bromides/chlorides, or formate brines are very expensive. In order to get the required cleaning/debris removal, large volumes are conventionally required. Some polycationic compounds of the present technology can be used as gelling agents for these expensive compounds to decrease the volumes required by decreasing the amount of expensive brines that leak off into the subterranean formation (often causing formation damage).

Subterranean formations have different properties, such as different permeability, that can affect the ways in which matters flow into and out of the formations. Certain chemicals can alter the permeability by forming gels that can block matter transport through more porous zones. The matter transport is then diverted to other zones, from which hydrocarbon may be recovered, or into which additional treatments may be applied (e.g. acidizing). Some polycationic compounds of the present technology can be used as gelling agents in such diversion fluids.

Certain polycationic compositions of the present technology can also be used as additives for various processes in hydrocarbon recovery, for example, in fluid loss control, corrosion inhibition, scale inhibition, clay stabilizing, drag reducing, demulsifying, gas hydrate control, etc.

Fluid loss additives, or filtrate-reducing agents, are often used to minimize the loss of process fluids into the formations during various processes, e.g. drilling or fracturing. This helps avoid certain types of formation damage and reduces the expense of lost process fluids, some of which have high cost. Conventionally, fluid loss prevention can be divided into three categories by mechanisms, where (1) macroscopic particles clog the formation pores to form a filter cake with reduced permeability, (2) microscopic particles form a gel in the boundary layer between the fluids and the porous formation, and (3) a chemical resin is injected and cured irreversibly in the formation. Some polycationic compounds of the present technology can be used as fluid loss additives that can form a gel in the boundary layer to prevent fluid loss.

Corrosion and scale deposition are the two of the most costly problems in oil industries. Corrosion may occur not just in stimulation and recovery operations, but in transport and refining operations also. Some polycationic quaternary ammonium compounds of the present technology can provide useful, new or improved compositions for corrosion inhibition across the various hydrocarbon related operations.

Scale deposition also occurs in various operations in the petroleum industry. Scales may contain carbonates of calcium and iron, sulfates of barium and strontium, iron oxides and sulfides, and magnesium salts. Scale inhibitors may act as thermodynamic inhibitors by reacting or complexing with scale forming substances so that a chemical equilibrium is established that suppresses crystal growth. Polyamines, quaternaries, aminosulfonates and aminophosphonates are a few examples of chemical classes of scale inhibitors. Surfactants may also act as scale inhibitors by suppressing the adherence of crystals to metal surfaces. Some polycationic compounds of the present technology provide useful, new or improved scale inhibitors in each of these classes.

It is known that swelling due to clay or shale hydration in subterranean formations is one of the most important causes for borehole instability. Clays may swell as a result of surface hydration, or from osmotic pressure due to cation concentration gradients between the clay and surrounding water. Some polycationic compounds of the present technology provide useful and new clay stabilizers that can inhibit or reduce shale hydration.

In oil field, chemical additives that can reduce drag are used, for example, in pipelines for liquid transportation, in drilling applications and in fracturing. The drag on a fluid as it flows through pipes or down bore holes limits the pressures that may be attained, increases equipment demands and costs, and increases energy demands. Certain cationic surfactants are known to be drag reducing agents, and viscoelasticity is also frequently associated with drag reduction. Polymers are also used as drag reducers, but when they are used, one serious problem in the effectiveness of drag reducers is the chain degradation of polymers by shear strains in turbulent flow. Some polycationic compounds of the present technology provide drag reducers which do not suffer the degradation by shear strains.

When crude oil is produced, most of it occurs emulsified with water. Chemical demulsifiers are used to separate the water from the hydrocarbons before transportation. At refineries, crude oil is sometimes emulsified in fresh water, followed by demulsification, to reduce the salt content of the crude oil. Some polycationic compositions of the present technology can provide useful, new or improved compositions that can be used as demulsifiers.

Further, the polycationic compositions of the present technology can also function as gas hydrate inhibitors, either as crystal inhibitors or through other mechanisms. Gas hydrates are types of clathrates in which water and hydrocarbons form crystalline addition compounds. The host compound, water, forms crystals, and the guest compound, hydrocarbons such as methane, are held in free spaces between the water crystals. Gas hydrates can form in pipelines, forming solid deposits that reduce pipe diameter or even clog them. Some polycationic quats of the present technology can inhibit the formation of gas hydrates.

The present technology will be better understood by reference to the following examples. These examples are provided to describe specific embodiments of the invention and to demonstrate how they work. By providing these specific examples, the inventors do not limit the scope of the invention. It will be understood by those skilled in the art that the full scope of the invention encompasses the subject matter defined by the claims concluding this specification, and any equivalents of the claims.

EXAMPLES

Example 1

Synthesis of Structurally Defined
SoyAPDMA-3(OH)-18APDMA

A 1000 ml 5-necked glass flask was charged with about 40 g of deionized (DI) water, about 91.4 g of 2-propanol, 179 g of stearamidopropyldimethylamine (SAPDMA) (482.5 mmol) and 91.8 g of para-toluenesulfonic acid ("PTSA") dihydrate (482.5 mmol). The mixture was mixed and heated to approximately 50° C. About 46 g (497 mmol) of epichlorohydrin was added to the reactor dropwise during 2 hours with the reactor still at approximately 50° C. The pH value of the reaction mixture changed from about 4.5 (when the addition of epichlorohydrin started) to about 4.85 (when the addition finished).

After holding the reaction mixture at approximately 50° C. for an additional 2 hours, the pH became 5.17. The temperature of the solution was then increased to approximately 70° C. About 173 g (482.5 mmol) of soyamidopropyldimethylamines (SoyAPDMA) were added dropwise to the reactor. The pH value of the reaction solution was monitored so that pH did not exceed 8.0. The SoyAPDMA charge was completed in 30 minutes, and the pH never exceeded 7.0 during that time. The solution was held at approximately 70° C. for 2 hours. The reaction solution was then cooled and left standing overnight before being sampled for free amine and amine hydrochloride as follows.

Titration with KOH followed by HCl revealed that the reaction mixture had an amine salt (as the chloride) content of about 4%. Free amine could not be titrated because tosylate interferes with titration by HCl. Instead, about 5 g epichlorohydrin was added to consume the unreacted amine salt. The reaction mixture was held for about 2 hours at approximately 70° C., and was then titrated again. The resultant content of amine salt (as chloride) was about 2%. The reaction mixture was cooled, and its pH value was 6.8. Several drops of 20% HCl were added until pH was about 6. Solids analysis on a moisture balance showed a solid content of about 60.2%.

This example produced a structurally defined Gemini quat (GQ) in which one amine mixture was saturated and the other was largely unsaturated.

Example 2

Synthesis of Symmetric HERAPDMA-GQ

About 119 g 2-propanol and 177.4 g of high erucic rapeseed amidopropyl-N,N-dimethylamine (HERAPDMA) were added to 1000 ml 5-necked flask. A mixture of about 24.3 g of a solution of 37% HCl by weight and 5.7 g water was added to the flask dropwise over approximately 15 minutes with vigorous stirring and air cooling to minimize heating. At the end of addition, the temperature of solution reached 55° C., and the pH was 7.2. The addition funnel well was rinsed with water, and then epichlorohydrin was added during a 90 minute period, and the pH was continuously monitored. The temperature of the solution when the epichlorohydrin addition started was approximately 50° C. The temperature of the reaction solution rose to approximately 67° C. over the first hour and then remained there for about another 45 minutes, after which the temperature began to drop. Heating was then provided to increase the temperature to about 70° C., and heating was held for 4 hours prior to being shut down.

A sample of the resultant reaction solution was titrated for amine hydrochloride and free amine. The result showed that the reaction solution contained 4.0% of salt and 3.07% of free amine by weight based on the total weight of the solution sample. An additional 10 g epichlorohydrin was added. After the reaction solution was held at 70° C. for approximately 2 hours, the heat was turned off. After another 2 hours, the resultant solution was sampled for free amine and amine salt again. It contained about 2% free amine and amine salt combined (1.01% and 0.98% respectively). The pH value was about 6.7. Several drops of 20% HCl were added to adjust the pH to about 5.5.

Example 3

Synthesis of HERAPDMA-PCC 167 g of the product of Example 2 containing 100 g (118 mmol) of HERAPDMA-GQ were stripped of water and alcohol solvent by distilling them from the solution under a vacuum on a thin-film rotary evaporator. Three portions of MEK solvent (100 g) were distilled from the mixture to obtain a water level of 0.3% (determined by Karl-Fisher titration). Then, about 17.5 g (118 mol) of o-phthalic anhydride were added to the mixture with about 12 g (121 mmol) triethylamine. The mixture was then held at reflux at about 88° C. for one hour. The anhydride dissolved within the first 15 minutes and a clear solution was attained.

After the mixture was held at reflux at about 88° C. for an hour, the solution was cooled. A small sample was taken and the solvent was evaporated from the sample. An IR spectrum of the dried residue clearly showed an ester signal but no anhydride signal was detectable.

The reaction mixture was again placed on a thin-film rotary evaporator and the excess triethylamine and a portion of the MEK were removed. A thick, cloudy mixture was obtained that was then diluted with about 45 g methanol to obtain a clear amber solution with a solids content of about 50.1%. This solution was then used for preparing viscoelastic gels.

Example 4

Synthesis of a Non-Gemini HERAPDMA Bis-Quat

About 50.6 g water, 84.2 g 2-propanol, and 145.8 g HERAPDMA were added to a 500 ml 5-necked flask with stirring, nitrogen, reflux and a pH probe. Next, about 40 g 37% HCl was added slowly to the mixture with vigorous stirring. The reaction mixture was heated to 50° C., and then about 38.3 g epichlorohydrin was added slowly during a period of approximately 45 minutes. The reaction mixture was then held at approximately 50° C. for 2 hours, and was then further heated to approximately 70° C. About 41.1 g triethylamine (TEA) was then charged slowly to the reaction mixture through the addition funnel. The pH value of the reaction mixture was monitored closely to ensure that it did not exceed 8.0. The TEA addition was completed in about 30 minutes, and the pH value did not exceed 7.8. The reaction mixture was then held at approximately 70° C. for 2 hours prior to being sampled for free amine and amine hydrochloride. The sampling showed that the resultant reaction mixture contained 3.2% free amine and 2.1% amine hydrochloride (as HERAPDMA and its salt).

Next, another 5 g of epichlorohydrin was added to the reaction mixture. The reaction mixture was held for another hour at 70° C., and then sampled for free amine and amine salt again. The result was essentially unchanged and showed that the mixture contained about 3.1% amine and 2.0% salt. The reaction mixture was cooled, and its pH was adjusted to 5.5 with several drops of 20% HCl at 40° C. The non-gemini HERAPDMA bis-quat produced can be represented by the following formula:

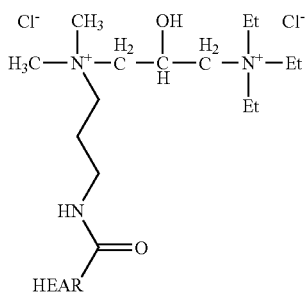

Comparative Example 5

Figure 5B:
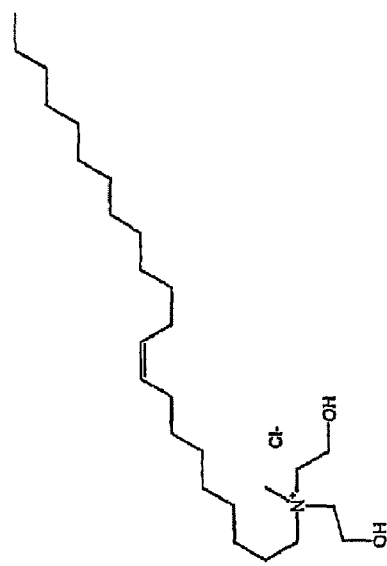
FIG. 5b shows a molecular structure of EHMAC.
Figure 5A:
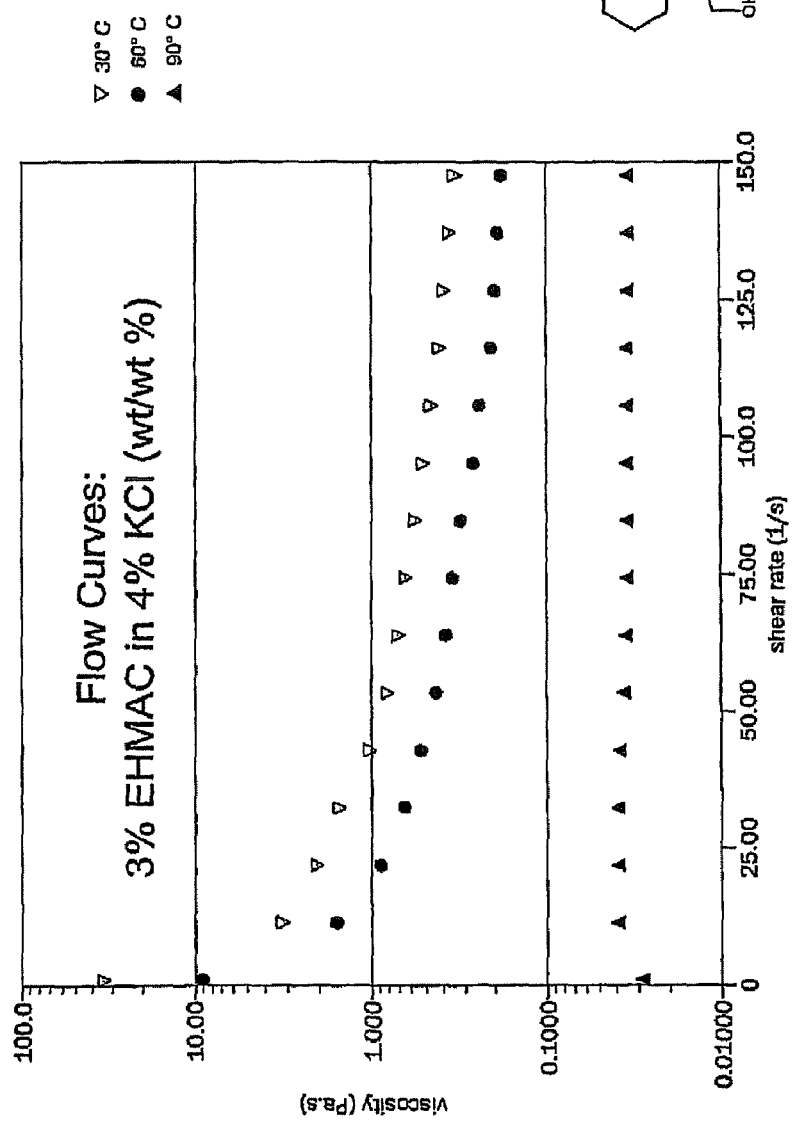
FIG. 5a shows flow curves of a VES containing 3% EHMAC in 4% KCl (wt/wt %).

In this comparison, 13 viscoelastic solutions were made from 8 polycationic quats of the present technology (Compounds 1-8 below), and were compared against a viscoelastic solution containing Schlumberger's commercially available cationic VES product ClearFRAC™ (EHMAC). The molecular structure of EHMAC is shown in FIG. 5b.

Figure 6B:
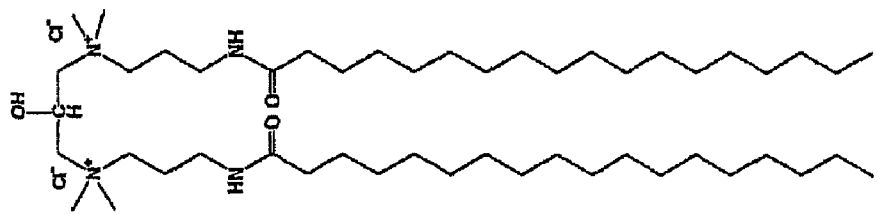
FIG. 6b shows a molecule structure of SAPDMA GQ.

The 8 compounds of the present technology that were used in this testing are as follows:

Compound 1 Gemini stearamidopropyldimethylammonium di-chloride (18APDMA-3(OH)-18-APDMA or SAPDMA GQ). (illustrated in FIG. 6b).

Compound 2 Gemini (cetyl/oleyl)amidopropyldimethylammonium di-chloride (16APDMA/18:1APDMA)-3-(OH)-(16APDMA/18:1APDMA). (illustrated in FIG. 7b, where R=$C_{14}H_{29}$ and $C_{16}H_{31}$ (linear)).

Compound 3 Dissymmetric gemini oleamidopropyldimethylammonium-stearamidopropyl-dimethylammonium di-chloride (18:1APDMA-3-(OH)-18-APDMA). (illustrated in FIG. 8b, where $R_1$=$C_{16}H_{33}$ (linear) and $R_2$=$C_{16}H_{31}$ (linear)).

Figure 9B:
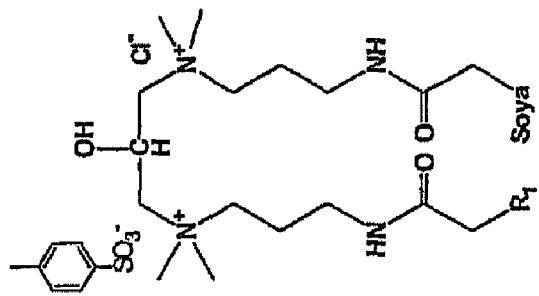
FIG. 9b shows a molecule structure of SoyAPDMA-3-(OH)-18APDMA.

Compound 4 Dissymmetric gemini soyamidopropyldimethylammonium-stearamidopropyl-dimethylammonium chloride toluene sulfonate (SoyAPDMA-3-(OH)-18APDMA). (illustrated in FIG. 9b, where $R_1$=$C_{16}H_{33}$ (linear)). SoyAPDMA is a mixture mostly of (in order of decreasing amounts): 18:2APDMA, 18:1APDMA, 16APDMA, 18:3APDMA, 18APDMA Compound 5 Gemini high erucic rapeseed amidopropyldimethylammonium di-chloride (HERAPDMA-3-(OH)-HERAPDMA or HERAPDMA GQ). (illustrated in FIG. 10b, where R is derived from high erucic rapeseed oil, in which at least 40% of fatty acid chains are erucyl). Common components of HERAPDMA include: 22:1APDMA, 18:2APDMA, 18:1APDMA and 18:3APDMA Compound 6 Dissymmetric gemini behenamidopropyldimethylammonium-high erucic rapeseed amidopropyldimethylammonium di-chloride (22APDMA-3-(OH)-HERAPDMA). (illustrated in FIG. 11b, where $R_1$ is derived from high erucic rapeseed oil, in which at least 40% of fatty acid chains are erucyl, and $R_2$=$C_{20}H_{41}$ (linear)). Common components of HERAPDMA include: 22:1APDMA, 18:2APDMA, 18:1APDMA and 18:3APDMA.

Figure 12B:
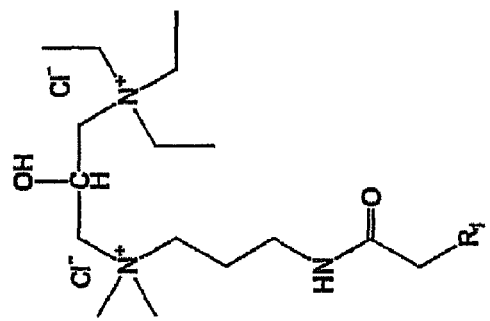
FIG. 12b shows a molecule structure of dissymmetric bis-quaternary (BQ) high erucic rapeseed amidopropyl-dimethylammonium-triethylammonium di-chloride.

Compound 7 Dissymmetric bis-Quaternary (BQ) high erucic rapeseed amidopropyl-dimethylammonium-triethylammonium di-chloride. (illustrated in FIG. 12b, where $R_1$ is derived from high erucic rapeseed oil, in which at least 40% of fatty acid chains are erucyl). Common components of HERAPDMA include: 22:1APDMA, 18:2APDMA, 18:1APDMA and 18:3APDMA.

Figure 13B:
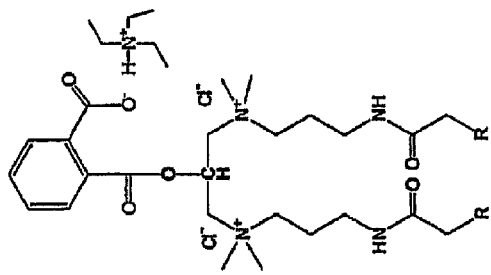
FIG. 13b shows a molecule structure of poly-cationic carboxylate (PCC) bis-high erucic rapeseed amidopropyldimethylammonium di-chloride phthalate half-ester, triethylammonium salt.

Compound 8 Poly-cationic carboxylate (PCC) bis-high erucic rapeseed amidopropyldimethylammonium di-chloride phthalate half-ester, triethylammonium salt. (illustrated in FIG. 13b, where R is derived from high erucic rapeseed oil, in which at least 40% of fatty acid chains are erucyl). Common components of HERAPDMA include: 22:1APDMA, 18:2APDMA, 18:1APDMA and 18:3APDMA.

The table below summarizes the viscoelastic gels prepared and tested in this example. One viscoelastic gel was made containing EHMAC. Additionally, one viscoelastic gel was made from each of Compounds 1, 2, 3, 6 and 8. Two viscoelastic gels, that differed in the weight percentage of the gellant and the additive, were made using each of Compounds 4 and 5. Three viscoelastic gels, that differed in the weight percentage of the gellant and the additive, were made using Compound 7.

Each viscoelastic gel was prepared by adding the specified weight percentages of compound (gellant) and additive to an electrolyte solution in a blender cup. The mixture was then blended on a commercial duty Waring blender for about from 1 to 3 minutes. Blends were made at room temperature, but the mechanical energy of the mixing process tended to warm them slightly. The resultant gel contained a large amount of entrained air, which was removed prior to rheology testing by centrifugation, heated ultrasonication, or combinations of both.

The electrolyte level for each viscoelastic composition is listed in the table below. In solutions for viscoelastic gels, tap water can be used as the solvent instead. The electrolyte solutions were prepared by mixing the salts with water and stirring a few minutes.

The viscoelastic solution containing EHMAC was prepared according to the description of U.S. Pat. No. 5,551,516, to Norman et al., at column 10, paragraph 35, through column 12, paragraph 40. The optimum salt concentration for highest viscosity with the EHMAC viscoelastic solution was determined to be about 4% KCl.

As indicated in the table above, each of the viscoelastic compositions of the present technology (with Compounds 1-8) provided higher viscosity than did EHMAC under the screening conditions. of the results illustrated in FIGS. 5a-13a also reveals unexpected and useful properties conferred by several of the embodiments of these inventions, including, for example:

Small or no decrease in viscosity as temperature increased across the range measured;
Lower requirements for gellant active ingredient;
Lower or no requirement for additives; or
Solubility and thickening of high salt concentration solutions.

Figure 6A:
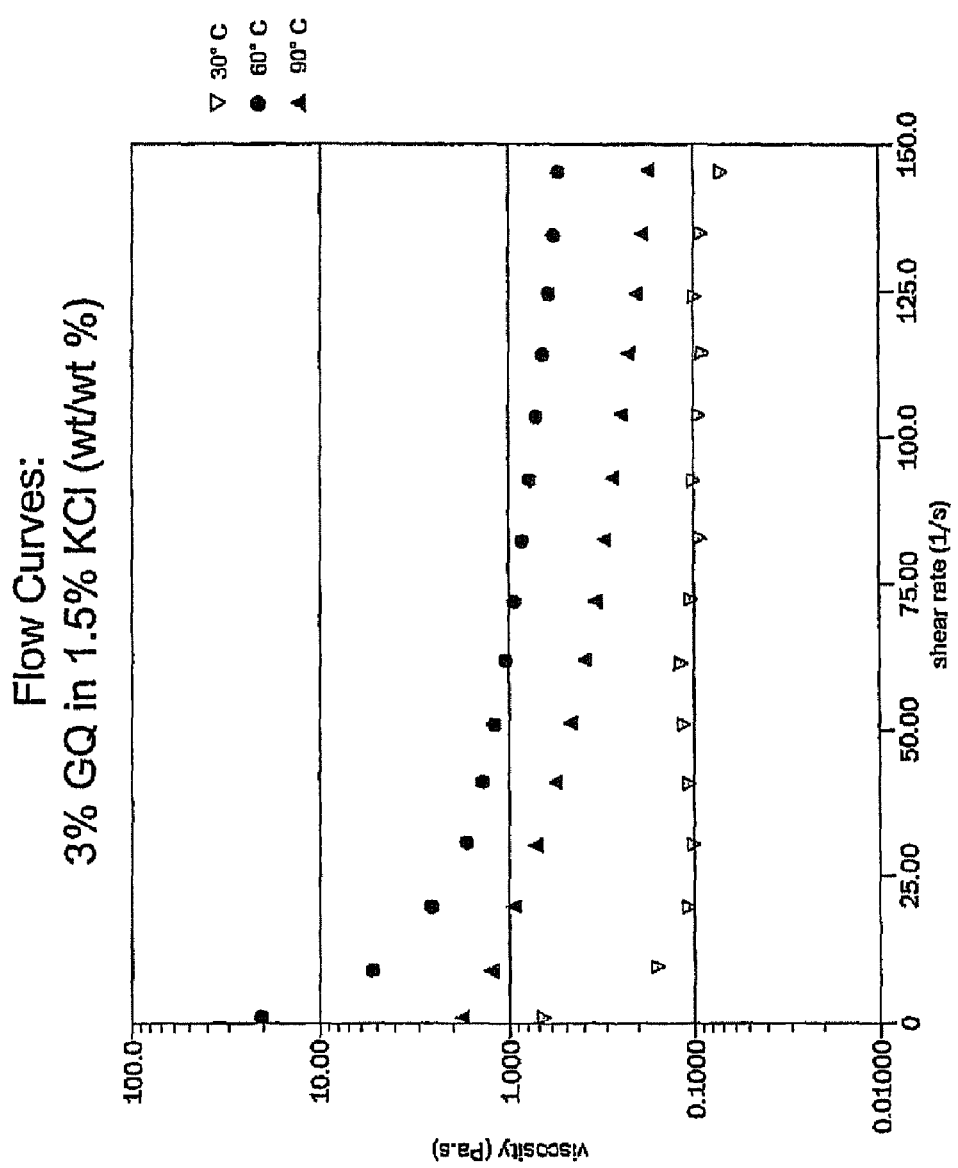
FIG. 6a shows flow curves of a VES containing 3% gemini stearamidopropyldimethyl-ammonium di-chloride (18APDMA-3(OH)-18-APDMA or SAPDMA GQ) in 1.5% KCl (wt/wt %).

Referring to FIG. 6a, Compound 1 of the present technology (SAPDMA GQ) demonstrated unexpected lower viscosity at 30° C. vs. 60° C. and 90° C. curves. The 90° C. viscosity of the SAPDMA GQ viscoelastic solution exceeded that of

| GELLANT COMPOUND | WT % GELLANT | ADDITIVE | WT % ADDITIVE (ELECTROLYTE) | SCREENING VISCOSITY (CP) | FIGURE |
|---|---|---|---|---|---|
| EHMAC | 3.00% | KCl | 4.00% | 35 | 5a |
| 1 | 3.00% | KCl | 1.50% | 250 | 6a |
| 2 | 3.00% | KCl | 1.50% | 60 | 7a |
| 3 | 3.00% | KCl | 1.50% | 293 | 8a |
| 4 | 3.00% | KCl | 0.75% | 317 | 9a |
| 4 | 1.25% | KCl | 1.50% | 74 | 9c |
| 5 | 3.00% | SXS | 0.50% | 169 | 10a |
| 5 | 2.00% | KCl | 1.50% | 168 | 10c |
| 6 | 3.00% | KCl | 2.00% | 276 | 11a |
| 7 | 4.00% | CaBr2 | 25.00% | 53 | 12a |
| 7 | 2.50% | CaBr2 | 25.00% | 125 | 12c |
| 7 | 2.75% | CaBr2 | 6.00% | 70 | 12d |
| 8 | 3.00% | none | none | 274 | 13a |

Screening viscosity was the viscosity at 90° C. and a shear rate of 100 sec$^{-1}$. This is referred to as the screening viscosity, because a guiding criterion for assessing gellants for fracturing processes is the viscosity of its gel at approximately 85° C. and a shear rate of 100 sec$^{-1}$. The generally accepted viscosity requirement for a VES under these conditions is about 100 cP (0.1 Pa·s).

Small amplitude oscillatory shear (SAOS) experiments were used to measure elastic properties of each of the viscoelastic compositions referenced in the table above. In this experiment, a sinusoidal imposed small strain was used to induce a sinusoidal measured stress and thus cause formation of shear-induced structures of gellant aggregates. The theory and methods are described in detail in *Dynamics of Surfactant Self-Assemblies* (Chapter 9; Surfactant Science Series Volume 125, editor Raul Zana). Each of the tested viscoelastic compositions was observed to posses elastic properties, i.e., the value of the elastic storage modulus (G') was equal to or greater than the value of the viscous loss modulus (G") at a frequency characteristic for each composition.

Measurements of the relationships between shear rate, viscosity and temperature that were made for each viscoelastic gel to create flow curves. The rheometer used for each of the tests was an AR2000 from TA Instruments. The geometry used was a DIN concentric cylinder. Viscosity was measured (approximately every 10 seconds) as the shear rate was stepped from 0.0015 to 150 sec$^{-1}$ over a period of approximately 3 minutes while the temperature was held constant. A flow curve was obtained at three temperatures (i.e., 30° C., 60° C. and 90° C.) for each sample. The Figures referenced in the table above illustrate the flow curves based upon those measurements.

the benchmark VES (illustrated in FIG. 5a) by more than 100% across the range of shear rates.

FIG. 7a shows that the VES of Compound 2 ((16APDMA/18:1APDMA)-3-(OH)-(16APDMA/18:1APDMA)) demonstrated an expected temperature—viscosity profile (decreasing viscosity with increasing temperature). The GQ VES viscosity at 90° C. (FIG. 7a) exceeded the viscosity of the 3% EHMAC VES at 90° C. (FIG. 5a) across the range of shear rates.

FIG. 8a shows that the VES of Compound 3 (18:1APDMA-3-(OH)-18APDMA) unexpectedly demonstrated very little temperature sensitivity from 30° C. to 90° C. This dissymmetric GQ VES had comparable viscosity to the VES of Compound 1 (SAPDMA GQ) at equal concentrations and temperatures, as shown by FIGS. 6a and 8a. However, unlike the SAPDMA GQ, which was a solid even at 45% actives in alcohol/water, this dissymmetric GQ of Compound 3 was a clear liquid at 60% actives in alcohol and water. Again, the viscosity of this VES exceeded that of the EHMAC VES substantially.

Figure 9A:
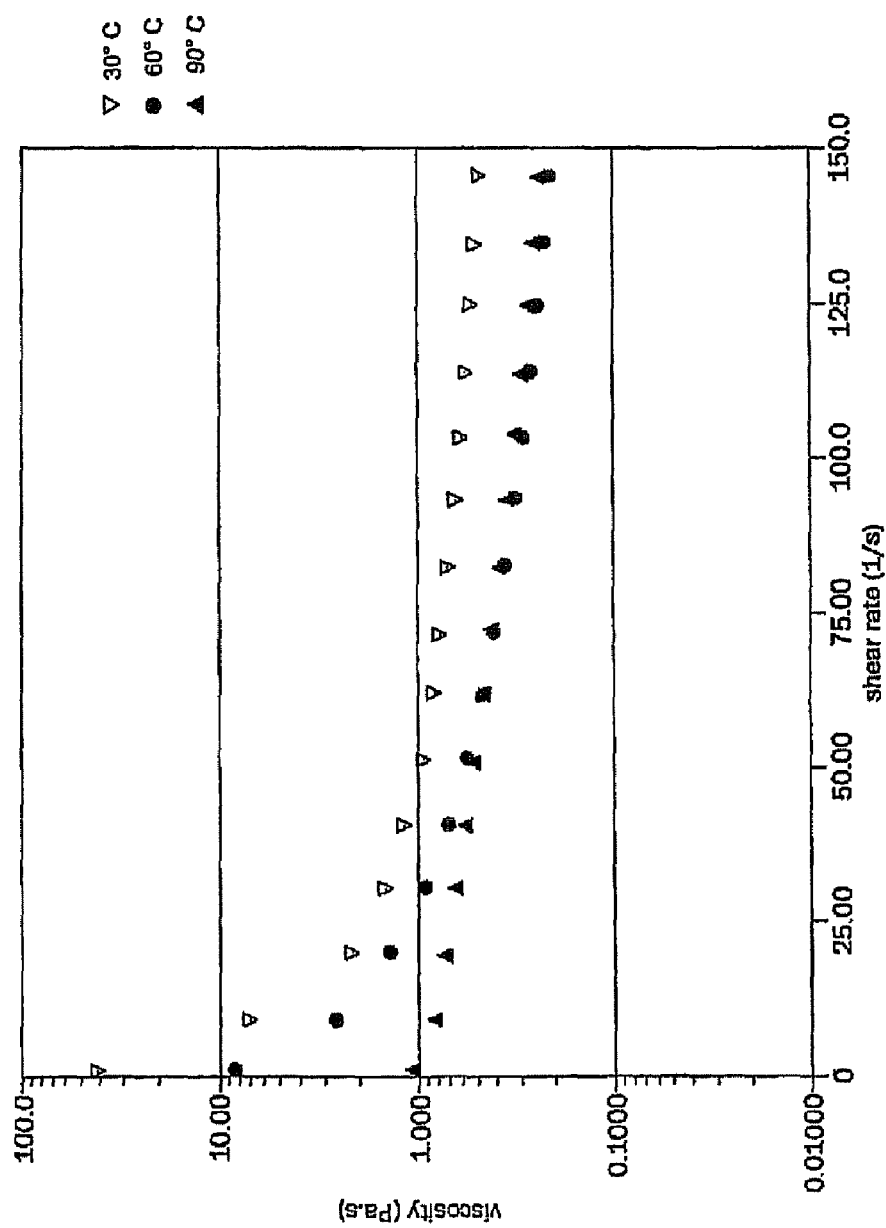
FIG. 9a shows flow curves of a VES containing 3% dissymmetric gemini soyamidopropyldimethylammonium-stearamidopropyl-dimethylammonium chloride toluene sulfonate (SoyAPDMA-3-(OH)-18APDMA) in 0.75% KCl (wt/wt %).

FIG. 9a shows the flow curves of the first viscoelastic solution prepared from Compound 4 (SoyAPDMA-3-(OH)-18APDMA), which was a 3% GQ solution in 0.75% KCl (wt/wt %). This VES showed a viscosity profile similar to that of the VES from Compound 3 (illustrated in FIGS. 8a and 9a). However, the benefit of a lower salt (KCl) requirement was achieved in Compound 4 through use of toluene sulfonic acid in place of hydrochloric acid in the synthesis. This VES with Compound 4 used less than 20% of the amount of KCl required by the EHMAC VES (illustrated in FIG. 5a), yet achieved superior results over the EHMAC VES. Like Compound 3, Compound 4 was obtained in an easily handled liquid at 60% actives.

Figure 9C:
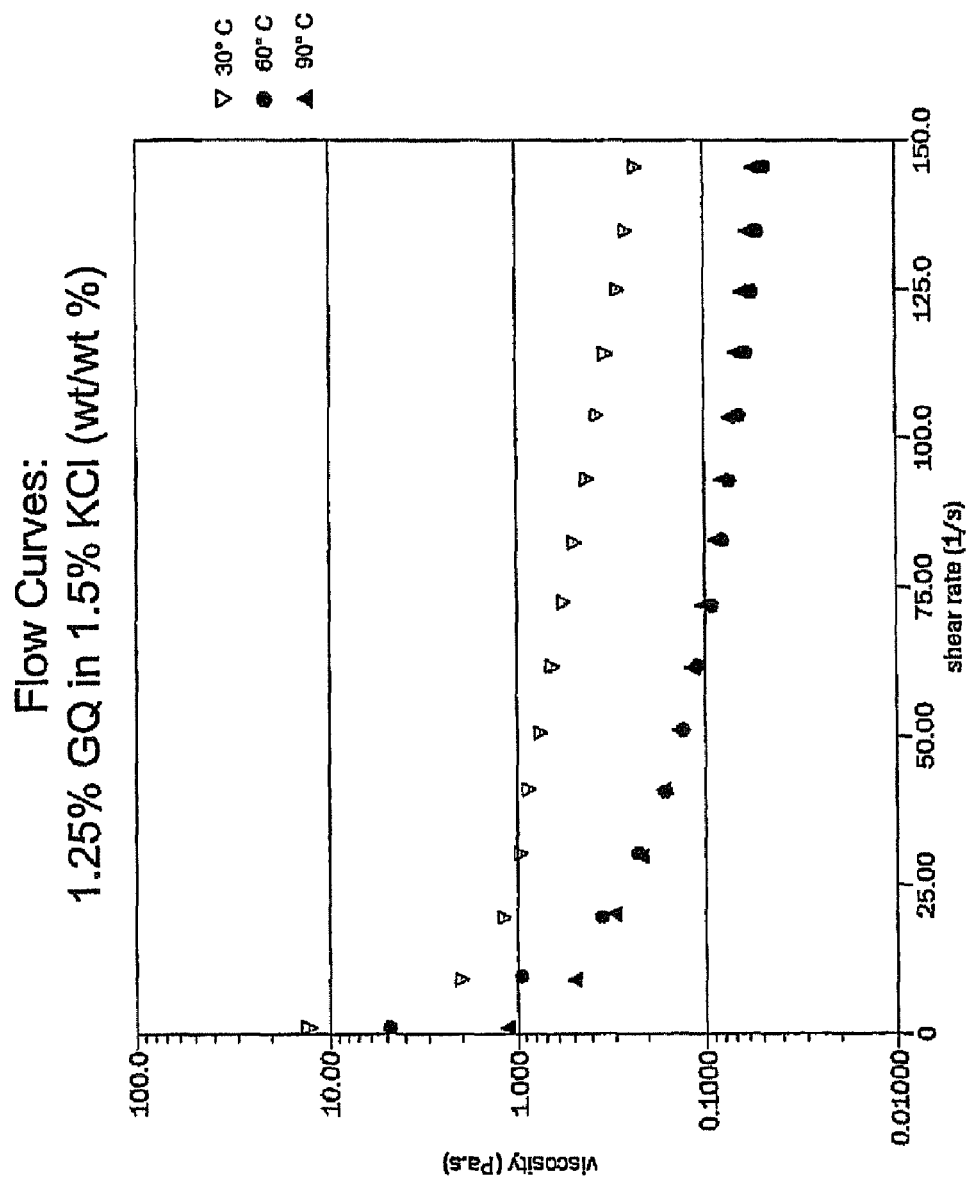
FIG. 9c shows flow curves of a VES containing 1.25% SoyAPDMA-3-(OH)-18APDMA in 1.5% KCl (wt/wt %).

FIG. 9c shows the flow curves of the second viscoelastic solution prepared from Compound 4, which contained 1.25% GQ in 1.5% KCl solution (wt/wt %). This second VES using Compound 4 demonstrated a substantially lower requirement for gellant when 1.5% KCl by weight was used. This VES from Compound 4 required less than 45% of the gellant and 50% less potassium chloride to obtain a viscosity profile superior to that of the EHMAC benchmark (illustrated in FIGS. 5a and 9c).

FIG. 10a shows the flow curves of the first viscoelastic solution prepared from Compound 5 (HERAPDMA GQ), which contained 3% GQ in a 0.5% sodium xylene sulfonate (SXS) solution (wt/wt %). HERAPDMA GQ was a liquid at 60% actives. An unexpected benefit demonstrated in this viscosity profile was a low sensitivity to temperature from about 30° C. to about 90° C.

The second VES based on HERAPDMA GQ (Compound 5) used 1.5% KCl in place of the SXS, and also used ⅔ the amount of gellant used in the EHMAC VES. The flow curves of this VES are shown in FIG. 10c. Again, the viscosity profile of this VES showed only small viscosity changes across the temperature range of about 30° C. to about 90° C.

FIG. 11a shows the flow curves for the viscoelastic solution prepared from Compound 6 (22APDMA-3-(OH)-HERAPDMA), which contained 3% GQ in a 2% KCl solution (wt/wt %). This VES based on Compound 6 provided viscosity more than triple that of the EHMAC VES at 90° C. across the range of shear rates (illustrated in FIGS. 5a and 11a).

Figure 12A:
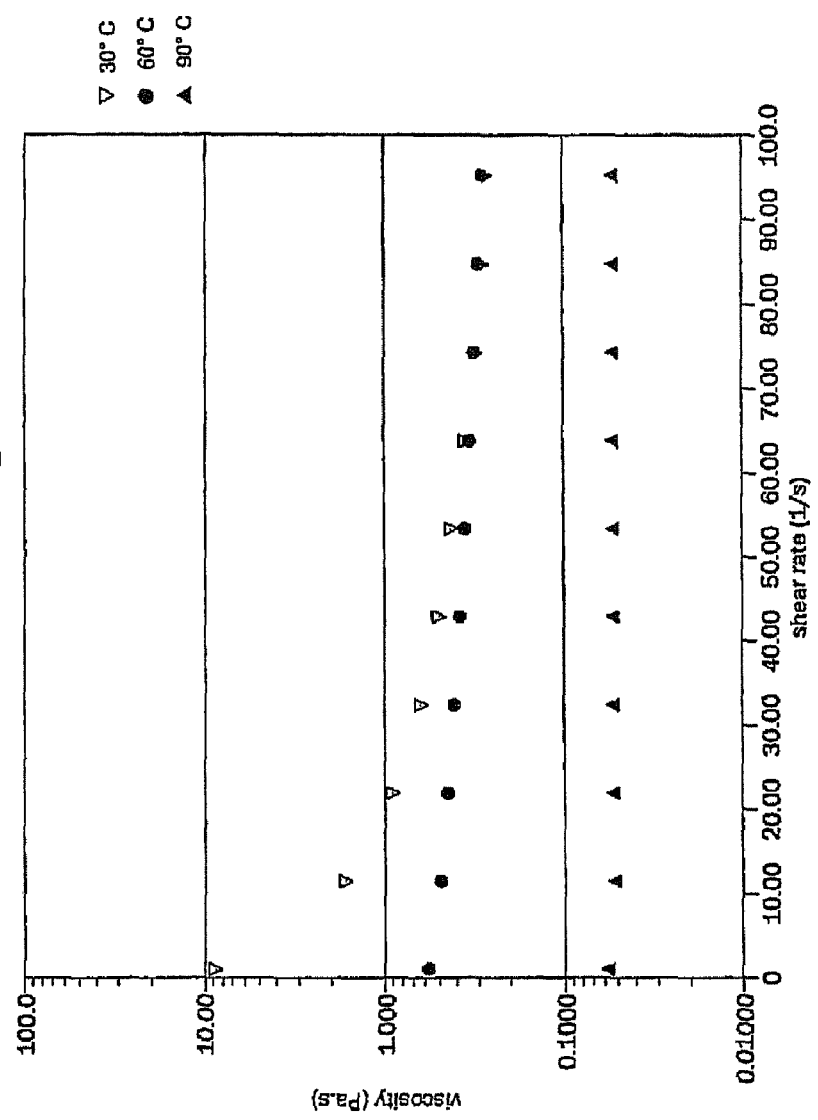
FIG. 12a shows flow curves of a VES containing 4% of the dissymmetric BQ shown in FIG. 12b in 25% $CaCl_2$ (wt/wt %).

FIG. 12a shows the flow curves of the first viscoelastic solution prepared from bis quat (BQ) Compound 7, which contained 4% BQ in a 25% CaCl$_2$ solution (wt/wt %). The density of 25% CaCl$_2$ at 25° C. was about 1.24 g/ml. The flow curves in FIG. 12a show that the single hydrophobe-bis-quaternary compound of the present technology provided useful VES properties in solutions with higher salt concentrations than used for the VESs of the GQs of the present technology or the EHMAC gellant. This example demonstrates that dissymmetric single hydrophobe BQs can confer VES properties in high density brines, which are commonly used in well bore service fluids for the benefits of their density and/or salt effects, where the EHMAC VES normally will fail.

Figure 12C:
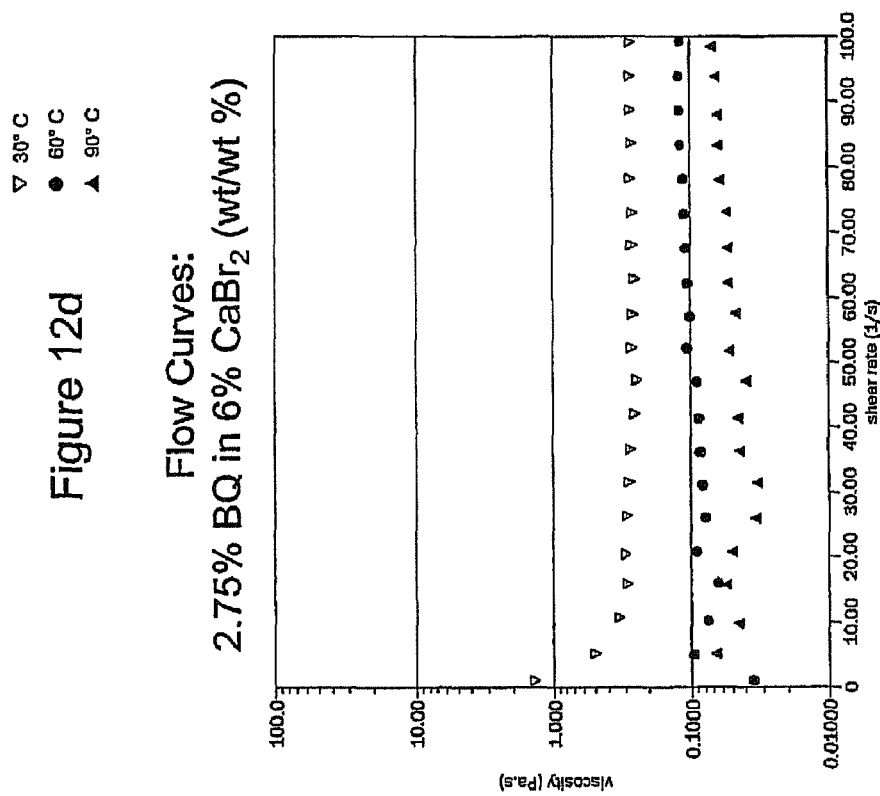
FIG. 12c shows flow curves of a VES containing 2.5% of the dissymmetric BQ shown in FIG. 12b in 25% $CaBr_2$ (wt/wt %).

The flow curves of a second VES from BQ Compound 7 are shown in FIG. 12c, which demonstrated an even higher viscosity than those shown in FIG. 12a. The second VES containing 2.5% BQ in a 25% CaBr$_2$ solution (wt/wt %) used less gellant than that of FIG. 12a and a different high density brine (25% CaBr$_2$ has a density of about 1.2 g/ml at 25° C.).

Thickening in high salt concentration solutions can be useful for a number of operations besides fracturing, as described earlier in this disclosure.

Figure 12D:
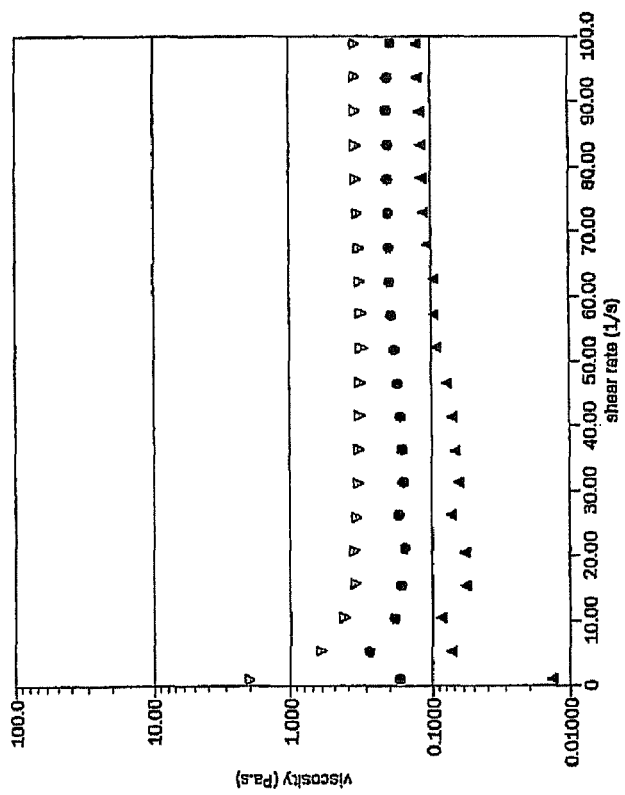
FIG. 12d shows flow curves of a VES containing 2.75% of the dissymmetric BQ shown in FIG. 12b in 6% $CaBr_2$ (wt/wt %).

Referring to FIG. 12d, the flow curves of a third VES prepared from BQ Compound 7 demonstrated that, besides high salt concentration solutions, dissymmetric single hydrophobe BQs can provide useful thickening properties across a wide range of salt concentrations. In this VES, a 6% CaBr$_2$ solution was used, which had a density of only about 1.05 g/ml at 25° C.

A gelled, viscoelastic high-density clear brine was also prepared from Compound 7, which contained 4% BQ in a solution of 52.8% ZnBr2, 22.8% CaBr2, and 24.4% water, and had a density of about 19 lb. per gallon at 70° C. Viscosity measurements were not obtained on this solution as the brine components were harmful to the rheometer.

Figure 13A:
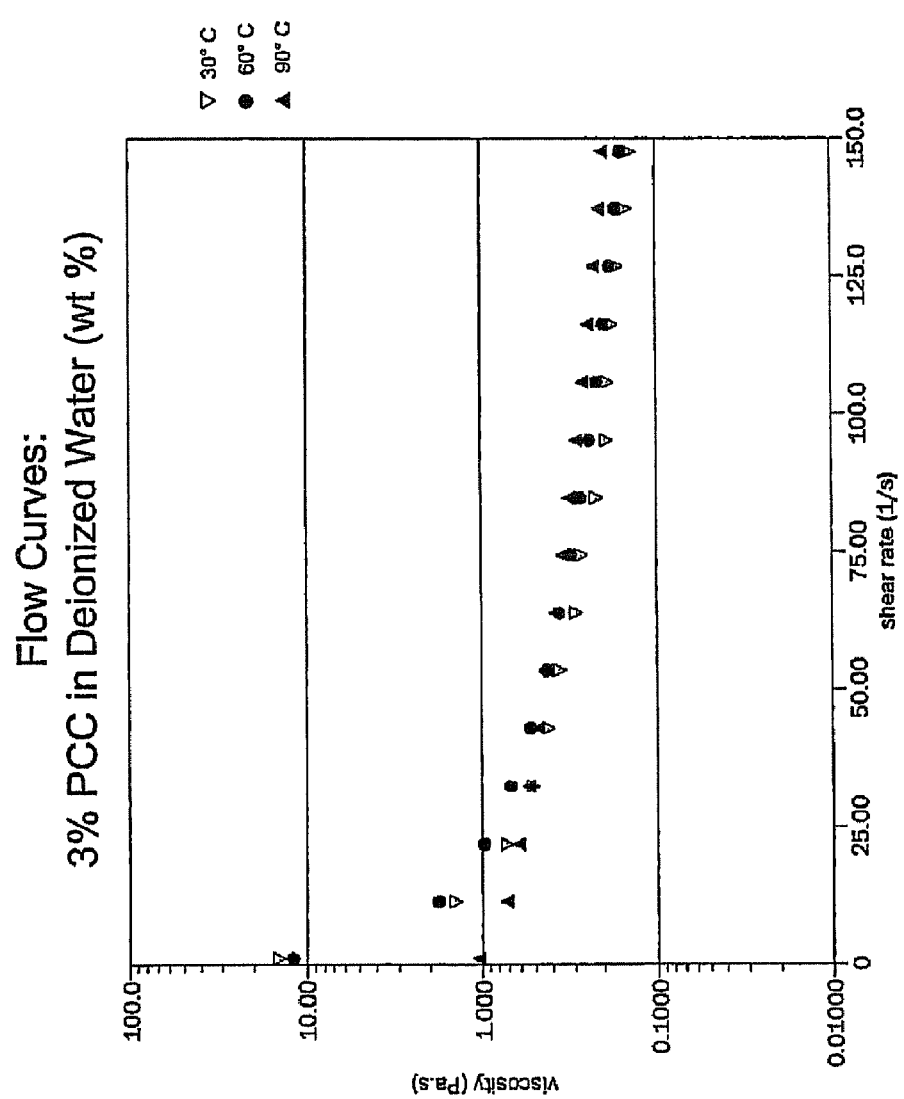
FIG. 13a shows flow curves of a VES containing 3% of the PCC shown in FIG. 13b in deionized water (wt %).

FIG. 13a shows the flow curves of a VES prepared from Compound 8, which was a PCC. This VES contained 3 wt % PCC in deionized water and no salt or other additive was added. The flow curves of this VES showed unexpected and useful results, because it completely eliminated the requirement for salts, cationic surfactants, or other additives. The viscosity profile for this VES also demonstrated very little change in viscosity over the temperature range of about 30° C. to about 90° C., and was at least 100% higher than that of the EHMAC VES (illustrated in FIGS. 5a and 13a).

Studying the flow curves of the viscoelastic solutions containing Compounds 1-8 of the present technology collectively, the relative insensitivity of viscosity to temperature across the range measured suggests that such compositions might provide useful thickening properties well above the range measured, especially in light of the degree to which they exceed the 100 cP viscosity target under the screening conditions.

The invention has been described above in such full, clear, concise and exact terms as to enable any person skilled in the art to which it pertains, to practice the same. It is to be understood that the foregoing describes preferred embodiments of the invention and that modifications may be made thereto without departing from the spirit or scope of the invention as set forth in the following claims.

What is claimed is:

1. A viscoelastic composition comprising water, at least one polycationic quaternary ammonium compound to control the viscoelasticity of the composition, wherein the at least one polycationic quaternary ammonium compound comprises a dissymmetric bis-quaternary compound of the following general formula:

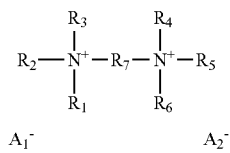

wherein $R_2$, $R_3$, $R_4$, $R_5$, and $R_6$ are members independently selected from the group consisting of:
  (a) hydrocarbyl groups having from about 1 to about 4 carbon atoms; and
  (b) substituted hydrocarbyl groups having from about 1 to about 4 carbon atoms;
wherein $R_7$ is a member selected from the group consisting of hydrocarbyl groups having from about 2 to about 30 carbon atoms, and substituted hydrocarbyl groups having from about 2 to about 30 carbon atoms;
wherein $R_1$ is a member selected from the group consisting of hydrocarbyl groups having from about 13 to about 40 carbon atoms or substituted hydrocarbyl groups having from about 13 to about 40 carbon atoms;
wherein $A_1^-$ and $A_2^-$ are independently selected from the group consisting of:
  (i) negatively charged inorganic ions;
  (ii) organic molecules with one or more negatively charged functional groups; and
  (iii) negatively charged functional groups which are part of $R_1$, $R_2$, $R_3$, $R_4$, $R_5$, $R_6$, or $R_7$;
the composition further comprising from about 5% to about 75% by weight of at least one inorganic salt;
wherein the viscoelastic composition provides viscoelasticity at a temperature of at least about 80° C.

2. The composition of claim 1, wherein the hydrocarbyl groups or substituted hydrocarbyl groups of $R_1$ comprise carboxamides, carboximides, polycarboxamides, polycarboximides, carboxamidines, carboximidines, carboxylic esters, polycarboxylic esters, carboxylic acids, polycarboxylic acids, carboxylates, polycarboxylates, or combinations thereof.

3. The composition of claim 1, wherein the substituted hydrocarbyl groups of group (b) have one or more substituents selected from the group consisting of hydroxy, alkoxy, aryloxy, carbonate ester, carbamate, sulfonate, phosphinate, phosphite, phosphate, phosphonate, and combinations thereof.

4. The composition of claim 3, wherein the alkoxy or aryloxy substituents have the general formula —OR, where R is a hydrocarbyl group having from about 1 to about 4 carbon atoms.

5. The composition of claim 1, wherein the substituted hydrocarbyl groups for $R_7$ have one or more substituents selected from the group consisting of hydroxyl, alkoxy, aryloxy, ester carbonate, carbamate, sulfonic acid, sulfonate, phosphinic acid, phosphinate, phosphorous acid, phosphite, phosphoric acid, phosphate, phosphonate and combinations thereof.

6. The composition of claim 5, wherein the alkoxy or aryloxy substituents have the general formula —OR, where R is a hydrocarbyl group having from about 1 to about 4 carbon atoms.

7. The composition of claim 1, wherein $R_7$ is derived from a substrate including two reactive sites with different reactivities.

8. The composition of claim 1, wherein $R_7$ is hydrophilic.

9. The composition of claim 1, wherein $R_7$ comprises hydrocarbyl groups having from about 3 to about 8 carbon atoms or substituted hydrocarbyl groups having from about 3 to about 8 carbon atoms.

10. The composition of claim 9, wherein $R_7$ has a linear configuration.

11. The composition of claim 1, wherein $R_7$ comprises hydrocarbyl groups having from about 9 to about 21 carbon atoms or substituted hydrocarbyl groups having from about 9 to about 21 carbon atoms.

12. The composition of claim 11, wherein $R_7$ has a configuration comprising a ring.

13. The composition of claim 1, wherein $R_7$ is derived from a di-haloalkyl hydrocarbon containing from about 2 to about 12 carbon atoms in which the two halogen atoms are attached to different primary or secondary saturated carbon atoms, and wherein the two halogen atoms have different reactivities.

14. The composition of claim 13, wherein the two halogen atoms are different.

15. The composition of claim 13, wherein the di-haloalkyl hydrocarbon is substituted with one or more additional hydroxy, alkoxy, or aryloxy substituents, and wherein the additional substituents are not attached to one of the halogen-bearing carbon atoms.

16. The composition of claim 13, wherein the di-haloalkyl hydrocarbon has a primary bromoalkyl group and a secondary chloroalkyl group.

17. The composition of claim 1, wherein $R_7$ is a substituted hydrocarbyl group that is not a hydroxyalkylene.

18. The composition of claim 1, wherein $R_7$ is derived from an epihalohydrin.

19. The composition of claim 1, wherein $R_1$ is derived from a carboxylic acid having from about 13 to about 40 carbon atoms.

20. The composition of claim 1, wherein each of $R_4$, $R_5$, and $R_6$ is a hydrocarbyl group having from about 1 to about 4 carbon atoms.

21. The composition of claim 1, wherein the at least one polycationic quaternary ammonium compound comprises less than about 10% by weight based on the total weight of the composition.

* * * * *